United States Patent [19]

Queener et al.

[11] Patent Number: 5,451,522

[45] Date of Patent: Sep. 19, 1995

[54] GENES ENCODING AND METHOD OF EXPRESSING AN ENZYME: PHTHALYL AMIDASE

[75] Inventors: Stephen W. Queener, Indianapolis; Joseph M. Zock, Greenwood, both of Ind.

[73] Assignee: Eli Lilly and Company, Indianapolis, Ind.

[21] Appl. No.: 275,490

[22] Filed: Jul. 15, 1994

[51] Int. Cl.$^6$ .......................... C12N 9/78; C12N 1/21; C12N 15/55

[52] U.S. Cl. ................... 435/252.3; 435/227; 435/228; 435/320.1; 435/252.33; 435/252.35; 536/23.2; 536/24.1

[58] Field of Search .................... 435/227, 228, 320.1, 435/252.3, 252.33, 252.35; 536/23.2, 24.1

[56] References Cited

U.S. PATENT DOCUMENTS 4,977,089 12/1990 Kovacevic et al. ............ 435/252.31
5,032,510 7/1991 Kovacevic et al. ............... 435/69.1

OTHER PUBLICATIONS

Smith, Gale E., et al., *Molecular and Cellular Biology*, vol. 3, No. 12, pp. 2156–2165, Dec. 1983.
Yang et al., *J. Biol. Chem.*, 268:10870, 1993.

*Primary Examiner*—Charles L. Patterson, Jr.
*Assistant Examiner*—Keith D. Hendricks
*Attorney, Agent, or Firm*—Paul R. Cantrell; David E. Boone; Gerald V. Dahling

[57] ABSTRACT

Phthalyl amidase is an enzyme previously unknown in the art that catalyzes removal of the phthalyl moiety from phthalyl-containing amides. The current invention provides DNA compounds encoding the phthalyl amidase enzyme and methods for expressing such compounds. The present invention also provides recombinant DNA vectors encoding phthalyl amidase and host cells transformed with these DNA vectors.

42 Claims, 2 Drawing Sheets

Function and restriction map of plasmid vector pZPA600.
Abbreviations:
PAorf = phthalyl amidase open reading frame.
tsr = gene enabling resistance to thiostrepton.

Function and restriction map of plasmid vector pZPA400.
Abbreviations:
PA-orf = phthalyl amidase open reading frame.
pL97-pro = modified promoter from phage lamda.
tet = gene enabling resistance to thiostrepton.
cI857 = gene encoding temperatrue sensitive lamda repressor.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
(A) LENGTH: 1359 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1356

(xi) SEQUENCE DESCRIPTION: SEQ ID NO:1:

```
CAG GCG CCG TCT GTG CAC CAA CAC GTC GCC TTC ACT GAG GAA ATT GGA       48
Gln Ala Pro Ser Val His Gln His Val Ala Phe Thr Glu Glu Ile Gly
 1               5                  10                  15

GAC CTT CCC GAC GGC TCA AGT TAC ATG ATC CGT GTG CCG GAG AAC TGG       96
Asp Leu Pro Asp Gly Ser Ser Tyr Met Ile Arg Val Pro Glu Asn Trp
            20                  25                  30

AAC GGC GTG TTA ATT CGC GAC CTA GAC CTT GTC AGC GGC ACC AGC AAT      144
Asn Gly Val Leu Ile Arg Asp Leu Asp Leu Val Ser Gly Thr Ser Asn
        35                  40                  45

TCT AAC GCC GCA AGG TAC GAA ACC ATG CTG AAA GAA GGT TTT GCC GTT      192
Ser Asn Ala Ala Arg Tyr Glu Thr Met Leu Lys Glu Gly Phe Ala Val
    50                  55                  60

GCT GGC ACG GCG AGG CAT CCC CTT CGG CAA TGG CAA TAT GAC CCC GCT      240
Ala Gly Thr Ala Arg His Pro Leu Arg Gln Trp Gln Tyr Asp Pro Ala
 65                  70                  75                  80

CAC GAG ATT GAA AAC CTC AAT CAC GTG CTG GAC ACA TTC GAG GAA AAT      288
His Glu Ile Glu Asn Leu Asn His Val Leu Asp Thr Phe Glu Glu Asn
                85                  90                  95
```

| | | | | | | | | | | | | | | | | |
|---|---|---|---|---|---|---|---|---|---|---|---|---|---|---|---|---|
| TAC | GGT | TCA | CCT | GAA | AGA | GTT | ATC | CAG | TAC | GGT | TGC | TCG | GGT | GGG | GCA | 336 |
| Tyr | Gly | Ser | Pro | Glu | Arg | Val | Ile | Gln | Tyr | Gly | Cys | Ser | Gly | Gly | Ala | |
| | | | 100 | | | | | 105 | | | | | 110 | | | |
| CAC | GTG | TCA | CTA | GCC | GTG | GCA | GAG | GAC | TTC | TCG | GAC | CGC | GTA | GAT | GGC | 384 |
| His | Val | Ser | Leu | Ala | Val | Ala | Glu | Asp | Phe | Ser | Asp | Arg | Val | Asp | Gly | |
| | | 115 | | | | | 120 | | | | | 125 | | | | |
| TCA | GTT | GCT | CTA | GCT | GCT | CAT | ACT | CCT | GTC | TGG | ATA | ATG | AAT | TCT | TTC | 432 |
| Ser | Val | Ala | Leu | Ala | Ala | His | Thr | Pro | Val | Trp | Ile | Met | Asn | Ser | Phe | |
| | 130 | | | | | 135 | | | | | 140 | | | | | |
| TTG | GAC | GGA | TGG | TTT | TCG | CTG | CAG | TCT | CTG | ATC | GGC | GAG | TAC | TAT | GTA | 480 |
| Leu | Asp | Gly | Trp | Phe | Ser | Leu | Gln | Ser | Leu | Ile | Gly | Glu | Tyr | Tyr | Val | |
| 145 | | | | | 150 | | | | | 155 | | | | | 160 | |
| GAA | GCT | GGT | CAC | GGC | CCA | CTT | TCG | GAT | CTC | GCT | ATT | ACG | AAA | CTG | CCC | 528 |
| Glu | Ala | Gly | His | Gly | Pro | Leu | Ser | Asp | Leu | Ala | Ile | Thr | Lys | Leu | Pro | |
| | | | | 165 | | | | | 170 | | | | | 175 | | |
| AAT | GAT | GGT | AGC | TCT | AAT | TCG | AGC | GGT | CAT | GGA | ATG | GAA | GGA | GAT | CTT | 576 |
| Asn | Asp | Gly | Ser | Ser | Asn | Ser | Ser | Gly | His | Gly | Met | Glu | Gly | Asp | Leu | |
| | | | 180 | | | | | 185 | | | | | 190 | | | |
| CCT | GCC | GCG | TGG | CGC | AAC | GCG | TTC | ACC | GCT | GCT | AAC | GCC | ACA | CCT | GAG | 624 |
| Pro | Ala | Ala | Trp | Arg | Asn | Ala | Phe | Thr | Ala | Ala | Asn | Ala | Thr | Pro | Glu | |
| | | 195 | | | | | 200 | | | | | 205 | | | | |
| GGT | CGC | GCA | CGC | ATG | GCA | CTA | GCC | TTT | GCG | CTC | GGT | CAG | TGG | TCT | CCG | 672 |
| Gly | Arg | Ala | Arg | Met | Ala | Leu | Ala | Phe | Ala | Leu | Gly | Gln | Trp | Ser | Pro | |
| | 210 | | | | | 215 | | | | | 220 | | | | | |
| TGG | TTG | GCC | GAC | AAC | ACG | CCC | CAA | CCT | GAT | CTC | GAT | GAT | CCT | GAG | GCC | 720 |
| Trp | Leu | Ala | Asp | Asn | Thr | Pro | Gln | Pro | Asp | Leu | Asp | Asp | Pro | Glu | Ala | |
| 225 | | | | | 230 | | | | | 235 | | | | | 240 | |
| ATC | GCG | GAT | TCC | GTA | TAT | GAG | TCT | GCC | ATG | CGA | CTT | GCA | GGA | AGC | CCT | 768 |
| Ile | Ala | Asp | Ser | Val | Tyr | Glu | Ser | Ala | Met | Arg | Leu | Ala | Gly | Ser | Pro | |
| | | | | 245 | | | | | 250 | | | | | 255 | | |
| GGG | GGA | GAA | GCG | CGC | ATA | ATG | TTC | GAG | AAC | GCC | GCT | CGA | GGG | CAA | CAG | 816 |
| Gly | Gly | Glu | Ala | Arg | Ile | Met | Phe | Glu | Asn | Ala | Ala | Arg | Gly | Gln | Gln | |
| | | | 260 | | | | | 265 | | | | | 270 | | | |
| CTC | TCT | TGG | AAC | GAC | GAC | ATC | GAC | TAT | GCG | GAT | TTC | TGG | GAG | AAC | TCA | 864 |
| Leu | Ser | Trp | Asn | Asp | Asp | Ile | Asp | Tyr | Ala | Asp | Phe | Trp | Glu | Asn | Ser | |
| | | 275 | | | | | 280 | | | | | 285 | | | | |
| AAC | CCA | GCC | ATG | AAG | AGC | GCC | GTT | CAG | GAG | CTG | TAC | GAC | ACG | GCC | GGC | 912 |
| Asn | Pro | Ala | Met | Lys | Ser | Ala | Val | Gln | Glu | Leu | Tyr | Asp | Thr | Ala | Gly | |
| | 290 | | | | | 295 | | | | | 300 | | | | | |
| CTT | GAT | CTG | CAG | TCC | GAT | ATA | GAA | ACG | GTA | AAT | TCC | CAG | CCA | CGC | ATA | 960 |
| Leu | Asp | Leu | Gln | Ser | Asp | Ile | Glu | Thr | Val | Asn | Ser | Gln | Pro | Arg | Ile | |
| 305 | | | | | 310 | | | | | 315 | | | | | 320 | |
| GAG | GCA | TCG | CAG | TAT | GCG | CTC | GAC | TAC | TGG | AAC | ACG | CCA | GGT | CGC | AAT | 1008 |
| Glu | Ala | Ser | Gln | Tyr | Ala | Leu | Asp | Tyr | Trp | Asn | Thr | Pro | Gly | Arg | Asn | |
| | | | | 325 | | | | | 330 | | | | | 335 | | |
| GTC | ATT | GGC | GAC | CCC | GAA | GTT | CCT | GTG | CTG | CGC | CTG | CAT | ATG | ATA | GGC | 1056 |
| Val | Ile | Gly | Asp | Pro | Glu | Val | Pro | Val | Leu | Arg | Leu | His | Met | Ile | Gly | |
| | | | 340 | | | | | 345 | | | | | 350 | | | |
| GAC | TAC | CAA | ATT | CCC | TAT | AGT | CTT | GTA | CAG | GGC | TAC | AGC | GAT | CTT | ATC | 1104 |
| Asp | Tyr | Gln | Ile | Pro | Tyr | Ser | Leu | Val | Gln | Gly | Tyr | Ser | Asp | Leu | Ile | |
| | | 355 | | | | | 360 | | | | | 365 | | | | |
| TCA | GAG | AAC | AAC | AAT | GAT | GAC | TTG | TAC | AGA | ACT | GCT | TTT | GTG | CAA | TCC | 1152 |
| Ser | Glu | Asn | Asn | Asn | Asp | Asp | Leu | Tyr | Arg | Thr | Ala | Phe | Val | Gln | Ser | |
| | 370 | | | | | 375 | | | | | 380 | | | | | |
| ACT | GGA | CAC | TGC | AAT | TTC | ACA | GCT | GCA | GAA | AGT | TCC | GCT | GCG | ATT | GAG | 1200 |
| Thr | Gly | His | Cys | Asn | Phe | Thr | Ala | Ala | Glu | Ser | Ser | Ala | Ala | Ile | Glu | |
| 385 | | | | | 390 | | | | | 395 | | | | | 400 | |
| GTC | ATG | ATG | CAA | CGG | CTT | GAC | ACG | GGT | GAG | TGG | CCG | AGC | ACC | GAG | CCG | 1248 |
| Val | Met | Met | Gln | Arg | Leu | Asp | Thr | Gly | Glu | Trp | Pro | Ser | Thr | Glu | Pro | |
| | | | | 405 | | | | | 410 | | | | | 415 | | |
| GAT | GAT | CTG | AAT | GCA | ATT | GCC | GAA | GCC | TCA | AAC | ACC | GGA | ACT | GAA | GCA | 1296 |
| Asp | Asp | Leu | Asn | Ala | Ile | Ala | Glu | Ala | Ser | Asn | Thr | Gly | Thr | Glu | Ala | |

|       |       |       |       | 420   |       |       |       |       | 425   |       |       |       |       | 430   |       |      |
|-------|-------|-------|-------|-------|-------|-------|-------|-------|-------|-------|-------|-------|-------|-------|-------|------|
| CGT   | TTC   | ATG   | GCC   | CTA   | GAT   | GGC   | TGG   | GAA   | ATA   | CCC   | GAG   | TAC   | AAT   | CGT   | ACT   | 1344 |
| Arg   | Phe   | Met   | Ala   | Leu   | Asp   | Gly   | Trp   | Glu   | Ile   | Pro   | Glu   | Tyr   | Asn   | Arg   | Thr   |      |
|       |       | 435   |       |       |       |       | 440   |       |       |       |       | 445   |       |       |       |      |

| TGG | AAG | CCT | GAA | TAA | 1359 |
|-----|-----|-----|-----|-----|------|
| Trp | Lys | Pro | Glu |     |      |
|     | 450 |     |     |     |      |

( 2 ) INFORMATION FOR SEQ ID NO:2:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Gln | Ala | Pro | Ser | Val | His | Gln | His | Val | Ala | Phe | Thr | Glu | Glu | Ile | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Leu | Pro | Asp | Gly | Ser | Ser | Tyr | Met | Ile | Arg | Val | Pro | Glu | Asn | Trp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Gly | Val | Leu | Ile | Arg | Asp | Leu | Asp | Leu | Val | Ser | Gly | Thr | Ser | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Asn | Ala | Ala | Arg | Tyr | Glu | Thr | Met | Leu | Lys | Glu | Gly | Phe | Ala | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ala | Gly | Thr | Ala | Arg | His | Pro | Leu | Arg | Gln | Trp | Gln | Tyr | Asp | Pro | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| His | Glu | Ile | Glu | Asn | Leu | Asn | His | Val | Leu | Asp | Thr | Phe | Glu | Glu | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Gly | Ser | Pro | Glu | Arg | Val | Ile | Gln | Tyr | Gly | Cys | Ser | Gly | Gly | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| His | Val | Ser | Leu | Ala | Val | Ala | Glu | Asp | Phe | Ser | Asp | Arg | Val | Asp | Gly |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Val | Ala | Leu | Ala | Ala | His | Thr | Pro | Val | Trp | Ile | Met | Asn | Ser | Phe |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Asp | Gly | Trp | Phe | Ser | Leu | Gln | Ser | Leu | Ile | Gly | Glu | Tyr | Tyr | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Glu | Ala | Gly | His | Gly | Pro | Leu | Ser | Asp | Leu | Ala | Ile | Thr | Lys | Leu | Pro |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asn | Asp | Gly | Ser | Ser | Asn | Ser | Ser | Gly | His | Gly | Met | Glu | Gly | Asp | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Ala | Ala | Trp | Arg | Asn | Ala | Phe | Thr | Ala | Ala | Asn | Ala | Thr | Pro | Glu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Gly | Arg | Ala | Arg | Met | Ala | Leu | Ala | Phe | Ala | Leu | Gly | Gln | Trp | Ser | Pro |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Trp | Leu | Ala | Asp | Asn | Thr | Pro | Gln | Pro | Asp | Leu | Asp | Asp | Pro | Glu | Ala |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ile | Ala | Asp | Ser | Val | Tyr | Glu | Ser | Ala | Met | Arg | Leu | Ala | Gly | Ser | Pro |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gly | Gly | Glu | Ala | Arg | Ile | Met | Phe | Glu | Asn | Ala | Ala | Arg | Gly | Gln | Gln |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Leu | Ser | Trp | Asn | Asp | Asp | Ile | Asp | Tyr | Ala | Asp | Phe | Trp | Glu | Asn | Ser |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Pro | Ala | Met | Lys | Ser | Ala | Val | Gln | Glu | Leu | Tyr | Asp | Thr | Ala | Gly |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Asp | Leu | Gln | Ser | Asp | Ile | Glu | Thr | Val | Asn | Ser | Gln | Pro | Arg | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

```
Glu  Ala  Ser  Gln  Tyr  Ala  Leu  Asp  Tyr  Trp  Asn  Thr  Pro  Gly  Arg  Asn
              325                     330                     335

Val  Ile  Gly  Asp  Pro  Glu  Val  Pro  Val  Leu  Arg  Leu  His  Met  Ile  Gly
                   340                     345                     350

Asp  Tyr  Gln  Ile  Pro  Tyr  Ser  Leu  Val  Gln  Gly  Tyr  Ser  Asp  Leu  Ile
              355                     360                     365

Ser  Glu  Asn  Asn  Asn  Asp  Asp  Leu  Tyr  Arg  Thr  Ala  Phe  Val  Gln  Ser
     370                     375                     380

Thr  Gly  His  Cys  Asn  Phe  Thr  Ala  Ala  Glu  Ser  Ser  Ala  Ala  Ile  Glu
385                     390                     395                          400

Val  Met  Met  Gln  Arg  Leu  Asp  Thr  Gly  Glu  Trp  Pro  Ser  Thr  Glu  Pro
                   405                     410                     415

Asp  Asp  Leu  Asn  Ala  Ile  Ala  Glu  Ala  Ser  Asn  Thr  Gly  Thr  Glu  Ala
              420                     425                     430

Arg  Phe  Met  Ala  Leu  Asp  Gly  Trp  Glu  Ile  Pro  Glu  Tyr  Asn  Arg  Thr
              435                     440                     445

Trp  Lys  Pro  Glu
          450
```

( 2 ) INFORMATION FOR SEQ ID NO:3:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1482

( x i ) SEQUENCE DESCRIPTION: SEQ ID NO:3:

```
ATG  ATA  ATC  AAG  GGT  AGT  GTA  CCG  GGT  AAA  GCC  GGA  GGA  AAA  CCT  CGA     48
Met  Ile  Ile  Lys  Gly  Ser  Val  Pro  Gly  Lys  Ala  Gly  Gly  Lys  Pro  Arg
  1             5                      10                      15

GCG  ACC  ATC  TTT  CAT  AGT  TCT  ATT  GCA  ACG  CTA  CTT  TTA  ACC  ACA  GTC     96
Ala  Thr  Ile  Phe  His  Ser  Ser  Ile  Ala  Thr  Leu  Leu  Leu  Thr  Thr  Val
              20                      25                      30

TCA  CTG  TCA  GGA  GTA  GCG  CCA  GCA  TTT  GCA  CAG  GCG  CCG  TCT  GTG  CAC    144
Ser  Leu  Ser  Gly  Val  Ala  Pro  Ala  Phe  Ala  Gln  Ala  Pro  Ser  Val  His
         35                      40                      45

CAA  CAC  GTC  GCC  TTC  ACT  GAG  GAA  ATT  GGA  GAC  CTT  CCC  GAC  GGC  TCA    192
Gln  His  Val  Ala  Phe  Thr  Glu  Glu  Ile  Gly  Asp  Leu  Pro  Asp  Gly  Ser
     50                      55                      60

AGT  TAC  ATG  ATC  CGT  GTG  CCG  GAG  AAC  TGG  AAC  GGC  GTG  TTA  ATT  CGC    240
Ser  Tyr  Met  Ile  Arg  Val  Pro  Glu  Asn  Trp  Asn  Gly  Val  Leu  Ile  Arg
 65                      70                      75                       80

GAC  CTA  GAC  CTT  GTC  AGC  GGC  ACC  AGC  AAT  TCT  AAC  GCC  GCA  AGG  TAC    288
Asp  Leu  Asp  Leu  Val  Ser  Gly  Thr  Ser  Asn  Ser  Asn  Ala  Ala  Arg  Tyr
                   85                      90                       95

GAA  ACC  ATG  CTG  AAA  GAA  GGT  TTT  GCC  GTT  GCT  GGC  ACG  GCG  AGG  CAT    336
Glu  Thr  Met  Leu  Lys  Glu  Gly  Phe  Ala  Val  Ala  Gly  Thr  Ala  Arg  His
              100                     105                     110

CCC  CTT  CGG  CAA  TGG  CAA  TAT  GAC  CCC  GCT  CAC  GAG  ATT  GAA  AAC  CTC    384
Pro  Leu  Arg  Gln  Trp  Gln  Tyr  Asp  Pro  Ala  His  Glu  Ile  Glu  Asn  Leu
         115                     120                     125

AAT  CAC  GTG  CTG  GAC  ACA  TTC  GAG  GAA  AAT  TAC  GGT  TCA  CCT  GAA  AGA    432
Asn  His  Val  Leu  Asp  Thr  Phe  Glu  Glu  Asn  Tyr  Gly  Ser  Pro  Glu  Arg
     130                     135                     140

GTT  ATC  CAG  TAC  GGT  TGC  TCG  GGT  GGG  GCA  CAC  GTG  TCA  CTA  GCC  GTG    480
Val  Ile  Gln  Tyr  Gly  Cys  Ser  Gly  Gly  Ala  His  Val  Ser  Leu  Ala  Val
```

| | | | | | | | | | | | | | | | | |
|---|---|---|---|---|---|---|---|---|---|---|---|---|---|---|---|---|
| 145 | | | | | 150 | | | | | 155 | | | | | 160 | |

| | | | | | | | | | | | | | | | | |
|---|---|---|---|---|---|---|---|---|---|---|---|---|---|---|---|---|
| GCA | GAG | GAC | TTC | TCG | GAC | CGC | GTA | GAT | GGC | TCA | GTT | GCT | CTA | GCT | GCT | 528 |
| Ala | Glu | Asp | Phe | Ser | Asp | Arg | Val | Asp | Gly | Ser | Val | Ala | Leu | Ala | Ala | |
| | | | | 165 | | | | | 170 | | | | | 175 | | |
| CAT | ACT | CCT | GTC | TGG | ATA | ATG | AAT | TCT | TTC | TTG | GAC | GGA | TGG | TTT | TCG | 576 |
| His | Thr | Pro | Val | Trp | Ile | Met | Asn | Ser | Phe | Leu | Asp | Gly | Trp | Phe | Ser | |
| | | | 180 | | | | | 185 | | | | | 190 | | | |
| CTG | CAG | TCT | CTG | ATC | GGC | GAG | TAC | TAT | GTA | GAA | GCT | GGT | CAC | GGC | CCA | 624 |
| Leu | Gln | Ser | Leu | Ile | Gly | Glu | Tyr | Tyr | Val | Glu | Ala | Gly | His | Gly | Pro | |
| | | | 195 | | | | | 200 | | | | | 205 | | | |
| CTT | TCG | GAT | CTC | GCT | ATT | ACG | AAA | CTG | CCC | AAT | GAT | GGT | AGC | TCT | AAT | 672 |
| Leu | Ser | Asp | Leu | Ala | Ile | Thr | Lys | Leu | Pro | Asn | Asp | Gly | Ser | Ser | Asn | |
| | 210 | | | | | 215 | | | | | 220 | | | | | |
| TCG | AGC | GGT | CAT | GGA | ATG | GAA | GGA | GAT | CTT | CCT | GCC | GCG | TGG | CGC | AAC | 720 |
| Ser | Ser | Gly | His | Gly | Met | Glu | Gly | Asp | Leu | Pro | Ala | Ala | Trp | Arg | Asn | |
| 225 | | | | | 230 | | | | | 235 | | | | | 240 | |
| GCG | TTC | ACC | GCT | GCT | AAC | GCC | ACA | CCT | GAG | GGT | CGC | GCA | CGC | ATG | GCA | 768 |
| Ala | Phe | Thr | Ala | Ala | Asn | Ala | Thr | Pro | Glu | Gly | Arg | Ala | Arg | Met | Ala | |
| | | | | 245 | | | | | 250 | | | | | 255 | | |
| CTA | GCC | TTT | GCG | CTC | GGT | CAG | TGG | TCT | CCG | TGG | TTG | GCC | GAC | AAC | ACG | 816 |
| Leu | Ala | Phe | Ala | Leu | Gly | Gln | Trp | Ser | Pro | Trp | Leu | Ala | Asp | Asn | Thr | |
| | | | 260 | | | | | 265 | | | | | 270 | | | |
| CCC | CAA | CCT | GAT | CTC | GAT | GAT | CCT | GAG | GCC | ATC | GCG | GAT | TCC | GTA | TAT | 864 |
| Pro | Gln | Pro | Asp | Leu | Asp | Asp | Pro | Glu | Ala | Ile | Ala | Asp | Ser | Val | Tyr | |
| | | 275 | | | | | 280 | | | | | 285 | | | | |
| GAG | TCT | GCC | ATG | CGA | CTT | GCA | GGA | AGC | CCT | GGG | GGA | GAA | GCG | CGC | ATA | 912 |
| Glu | Ser | Ala | Met | Arg | Leu | Ala | Gly | Ser | Pro | Gly | Gly | Glu | Ala | Arg | Ile | |
| | 290 | | | | | 295 | | | | | 300 | | | | | |
| ATG | TTC | GAG | AAC | GCC | GCT | CGA | GGG | CAA | CAG | CTC | TCT | TGG | AAC | GAC | GAC | 960 |
| Met | Phe | Glu | Asn | Ala | Ala | Arg | Gly | Gln | Gln | Leu | Ser | Trp | Asn | Asp | Asp | |
| 305 | | | | | 310 | | | | | 315 | | | | | 320 | |
| ATC | GAC | TAT | GCG | GAT | TTC | TGG | GAG | AAC | TCA | AAC | CCA | GCC | ATG | AAG | AGC | 1008 |
| Ile | Asp | Tyr | Ala | Asp | Phe | Trp | Glu | Asn | Ser | Asn | Pro | Ala | Met | Lys | Ser | |
| | | | | 325 | | | | | 330 | | | | | 335 | | |
| GCC | GTT | CAG | GAG | CTG | TAC | GAC | ACG | GCC | GGC | CTT | GAT | CTG | CAG | TCC | GAT | 1056 |
| Ala | Val | Gln | Glu | Leu | Tyr | Asp | Thr | Ala | Gly | Leu | Asp | Leu | Gln | Ser | Asp | |
| | | | 340 | | | | | 345 | | | | | 350 | | | |
| ATA | GAA | ACG | GTA | AAT | TCC | CAG | CCA | CGC | ATA | GAG | GCA | TCG | CAG | TAT | GCG | 1104 |
| Ile | Glu | Thr | Val | Asn | Ser | Gln | Pro | Arg | Ile | Glu | Ala | Ser | Gln | Tyr | Ala | |
| | | 355 | | | | | 360 | | | | | 365 | | | | |
| CTC | GAC | TAC | TGG | AAC | ACG | CCA | GGT | CGC | AAT | GTC | ATT | GGC | GAC | CCC | GAA | 1152 |
| Leu | Asp | Tyr | Trp | Asn | Thr | Pro | Gly | Arg | Asn | Val | Ile | Gly | Asp | Pro | Glu | |
| | 370 | | | | | 375 | | | | | 380 | | | | | |
| GTT | CCT | GTG | CTG | CGC | CTG | CAT | ATG | ATA | GGC | GAC | TAC | CAA | ATT | CCC | TAT | 1200 |
| Val | Pro | Val | Leu | Arg | Leu | His | Met | Ile | Gly | Asp | Tyr | Gln | Ile | Pro | Tyr | |
| 385 | | | | | 390 | | | | | 395 | | | | | 400 | |
| AGT | CTT | GTA | CAG | GGC | TAC | AGC | GAT | CTT | ATC | TCA | GAG | AAC | AAC | AAT | GAT | 1248 |
| Ser | Leu | Val | Gln | Gly | Tyr | Ser | Asp | Leu | Ile | Ser | Glu | Asn | Asn | Asn | Asp | |
| | | | | 405 | | | | | 410 | | | | | 415 | | |
| GAC | TTG | TAC | AGA | ACT | GCT | TTT | GTG | CAA | TCC | ACT | GGA | CAC | TGC | AAT | TTC | 1296 |
| Asp | Leu | Tyr | Arg | Thr | Ala | Phe | Val | Gln | Ser | Thr | Gly | His | Cys | Asn | Phe | |
| | | | 420 | | | | | 425 | | | | | 430 | | | |
| ACA | GCT | GCA | GAA | AGT | TCC | GCT | GCG | ATT | GAG | GTC | ATG | ATG | CAA | CGG | CTT | 1344 |
| Thr | Ala | Ala | Glu | Ser | Ser | Ala | Ala | Ile | Glu | Val | Met | Met | Gln | Arg | Leu | |
| | | 435 | | | | | 440 | | | | | 445 | | | | |
| GAC | ACG | GGT | GAG | TGG | CCG | AGC | ACC | GAG | CCG | GAT | GAT | CTG | AAT | GCA | ATT | 1392 |
| Asp | Thr | Gly | Glu | Trp | Pro | Ser | Thr | Glu | Pro | Asp | Asp | Leu | Asn | Ala | Ile | |
| | 450 | | | | | 455 | | | | | 460 | | | | | |
| GCC | GAA | GCC | TCA | AAC | ACC | GGA | ACT | GAA | GCA | CGT | TTC | ATG | GCC | CTA | GAT | 1440 |
| Ala | Glu | Ala | Ser | Asn | Thr | Gly | Thr | Glu | Ala | Arg | Phe | Met | Ala | Leu | Asp | |
| 465 | | | | | 470 | | | | | 475 | | | | | 480 | |

```
GGC  TGG  GAA  ATA  CCC  GAG  TAC  AAT  CGT  ACT  TGG  AAG  CCT  GAA  TAA              1485
Gly  Trp  Glu  Ile  Pro  Glu  Tyr  Asn  Arg  Thr  Trp  Lys  Pro  Glu
               485                           490
```

( 2 ) INFORMATION FOR SEQ ID NO:4:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ile  Ile  Lys  Gly  Ser  Val  Pro  Gly  Lys  Ala  Gly  Gly  Lys  Pro  Arg
 1              5                        10                       15

Ala  Thr  Ile  Phe  His  Ser  Ser  Ile  Ala  Thr  Leu  Leu  Leu  Thr  Thr  Val
               20                        25                       30

Ser  Leu  Ser  Gly  Val  Ala  Pro  Ala  Phe  Ala  Gln  Ala  Pro  Ser  Val  His
               35                        40                       45

Gln  His  Val  Ala  Phe  Thr  Glu  Glu  Ile  Gly  Asp  Leu  Pro  Asp  Gly  Ser
          50                        55                       60

Ser  Tyr  Met  Ile  Arg  Val  Pro  Glu  Asn  Trp  Asn  Gly  Val  Leu  Ile  Arg
65                       70                       75                       80

Asp  Leu  Asp  Leu  Val  Ser  Gly  Thr  Ser  Asn  Ser  Asn  Ala  Ala  Arg  Tyr
               85                        90                       95

Glu  Thr  Met  Leu  Lys  Glu  Gly  Phe  Ala  Val  Ala  Gly  Thr  Ala  Arg  His
               100                       105                      110

Pro  Leu  Arg  Gln  Trp  Gln  Tyr  Asp  Pro  Ala  His  Glu  Ile  Glu  Asn  Leu
               115                       120                      125

Asn  His  Val  Leu  Asp  Thr  Phe  Glu  Glu  Asn  Tyr  Gly  Ser  Pro  Glu  Arg
          130                       135                      140

Val  Ile  Gln  Tyr  Gly  Cys  Ser  Gly  Ala  His  Val  Ser  Leu  Ala  Val
145                      150                      155                      160

Ala  Glu  Asp  Phe  Ser  Asp  Arg  Val  Asp  Gly  Ser  Val  Ala  Leu  Ala  Ala
               165                       170                      175

His  Thr  Pro  Val  Trp  Ile  Met  Asn  Ser  Phe  Leu  Asp  Gly  Trp  Phe  Ser
               180                       185                      190

Leu  Gln  Ser  Leu  Ile  Gly  Glu  Tyr  Tyr  Val  Glu  Ala  Gly  His  Gly  Pro
               195                       200                      205

Leu  Ser  Asp  Leu  Ala  Ile  Thr  Lys  Leu  Pro  Asn  Asp  Gly  Ser  Ser  Asn
               210                       215                      220

Ser  Ser  Gly  His  Gly  Met  Glu  Gly  Asp  Leu  Pro  Ala  Ala  Trp  Arg  Asn
225                      230                       235                      240

Ala  Phe  Thr  Ala  Ala  Asn  Ala  Thr  Pro  Glu  Gly  Arg  Ala  Arg  Met  Ala
               245                       250                      255

Leu  Ala  Phe  Ala  Leu  Gly  Gln  Trp  Ser  Pro  Trp  Leu  Ala  Asp  Asn  Thr
               260                       265                      270

Pro  Gln  Pro  Asp  Leu  Asp  Asp  Pro  Glu  Ala  Ile  Ala  Asp  Ser  Val  Tyr
               275                       280                      285

Glu  Ser  Ala  Met  Arg  Leu  Ala  Gly  Ser  Pro  Gly  Gly  Glu  Ala  Arg  Ile
     290                       295                      300

Met  Phe  Glu  Asn  Ala  Ala  Arg  Gly  Gln  Gln  Leu  Ser  Trp  Asn  Asp  Asp
305                      310                       315                      320

Ile  Asp  Tyr  Ala  Asp  Phe  Trp  Glu  Asn  Ser  Asn  Pro  Ala  Met  Lys  Ser
               325                       330                      335

Ala  Val  Gln  Glu  Leu  Tyr  Asp  Thr  Ala  Gly  Leu  Asp  Leu  Gln  Ser  Asp
               340                       345                      350
```

|   |   |   |   |   |   |   |   |   |   |   |   |   |   |   |   |
|---|---|---|---|---|---|---|---|---|---|---|---|---|---|---|---|
| Ile | Glu | Thr 355 | Val | Asn | Ser | Gln | Pro 360 | Arg | Ile | Glu | Ala | Ser 365 | Gln | Tyr | Ala |
| Leu | Asp | Tyr 370 | Trp | Asn | Thr | Pro 375 | Gly | Arg | Asn | Val | Ile 380 | Gly | Asp | Pro | Glu |
| Val 385 | Pro | Val | Leu | Arg | Leu 390 | His | Met | Ile | Gly | Asp 395 | Tyr | Gln | Ile | Pro | Tyr 400 |
| Ser | Leu | Val | Gln | Gly 405 | Tyr | Ser | Asp | Leu | Ile 410 | Ser | Glu | Asn | Asn | Asn 415 | Asp |
| Asp | Leu | Tyr | Arg 420 | Thr | Ala | Phe | Val | Gln 425 | Ser | Thr | Gly | His | Cys 430 | Asn | Phe |
| Thr | Ala | Ala 435 | Glu | Ser | Ser | Ala | Ala 440 | Ile | Glu | Val | Met | Met 445 | Gln | Arg | Leu |
| Asp | Thr | Gly 450 | Glu | Trp | Pro | Ser 455 | Thr | Glu | Pro | Asp | Asp 460 | Leu | Asn | Ala | Ile |
| Ala 465 | Glu | Ala | Ser | Asn | Thr 470 | Gly | Thr | Glu | Ala | Arg 475 | Phe | Met | Ala | Leu | Asp 480 |
| Gly | Trp | Glu | Ile | Pro 485 | Glu | Tyr | Asn | Arg | Thr 490 | Trp | Lys | Pro | Glu |   |   |

(2) INFORMATION FOR SEQ ID NO:5:

(i) SEQUENCE CHARACTERISTICS:
(A) LENGTH: 1620 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 136..1617

(xi) SEQUENCE DESCRIPTION: SEQ ID NO:5:

```
GGATCCTTAG GAATCTAAAC ATTCTGGTTG ACACTCCACA TTTTGAATGT CAGCATTTCG      60

GCCATGGCTG CTATGCAGCC TGTTATTGCA TTTGAAATGG AATAGATCAG CAAACTTATC    120

GGGAGGATGA GTATT ATG ATA ATC AAG GGT AGT GTA CCG GGT AAA GCC GGA    171
                Met Ile Ile Lys Gly Ser Val Pro Gly Lys Ala Gly
                 1               5                   10

GGA AAA CCT CGA GCG ACC ATC TTT CAT AGT TCT ATT GCA ACG CTA CTT    219
Gly Lys Pro Arg Ala Thr Ile Phe His Ser Ser Ile Ala Thr Leu Leu
         15                  20                  25

TTA ACC ACA GTC TCA CTG TCA GGA GTA GCG CCA GCA TTT GCA CAG GCG    267
Leu Thr Thr Val Ser Leu Ser Gly Val Ala Pro Ala Phe Ala Gln Ala
     30                  35                  40

CCG TCT GTG CAC CAA CAC GTC GCC TTC ACT GAG GAA ATT GGA GAC CTT    315
Pro Ser Val His Gln His Val Ala Phe Thr Glu Glu Ile Gly Asp Leu
 45                  50                  55                  60

CCC GAC GGC TCA AGT TAC ATG ATC CGT GTG CCG GAG AAC TGG AAC GGC    363
Pro Asp Gly Ser Ser Tyr Met Ile Arg Val Pro Glu Asn Trp Asn Gly
                 65                  70                  75

GTG TTA ATT CGC GAC CTA GAC CTT GTC AGC GGC ACC AGC AAT TCT AAC    411
Val Leu Ile Arg Asp Leu Asp Leu Val Ser Gly Thr Ser Asn Ser Asn
             80                  85                  90

GCC GCA AGG TAC GAA ACC ATG CTG AAA GAA GGT TTT GCC GTT GCT GGC    459
Ala Ala Arg Tyr Glu Thr Met Leu Lys Glu Gly Phe Ala Val Ala Gly
         95                 100                 105

ACG GCG AGG CAT CCC CTT CGG CAA TGG CAA TAT GAC CCC GCT CAC GAG    507
Thr Ala Arg His Pro Leu Arg Gln Trp Gln Tyr Asp Pro Ala His Glu
    110                 115                 120

ATT GAA AAC CTC AAT CAC GTG CTG GAC ACA TTC GAG GAA AAT TAC GGT    555
Ile Glu Asn Leu Asn His Val Leu Asp Thr Phe Glu Glu Asn Tyr Gly
```

| | | | | | | | | | | | | | | | | |
|---|---|---|---|---|---|---|---|---|---|---|---|---|---|---|---|---|
| 125 | | | | | 130 | | | | | 135 | | | | | 140 | |
| TCA | CCT | GAA | AGA | GTT | ATC | CAG | TAC | GGT | TGC | TCG | GGT | GGG | GCA | CAC | GTG | 603 |
| Ser | Pro | Glu | Arg | Val 145 | Ile | Gln | Tyr | Gly | Cys 150 | Ser | Gly | Gly | Ala | His 155 | Val | |
| TCA | CTA | GCC | GTG | GCA | GAG | GAC | TTC | TCG | GAC | CGC | GTA | GAT | GGC | TCA | GTT | 651 |
| Ser | Leu | Ala | Val | Ala 160 | Glu | Asp | Phe | Ser | Asp 165 | Arg | Val | Asp | Gly | Ser 170 | Val | |
| GCT | CTA | GCT | GCT | CAT | ACT | CCT | GTC | TGG | ATA | ATG | AAT | TCT | TTC | TTG | GAC | 699 |
| Ala | Leu | Ala | Ala | His 175 | Thr | Pro | Val | Trp | Ile 180 | Met | Asn | Ser | Phe | Leu 185 | Asp | |
| GGA | TGG | TTT | TCG | CTG | CAG | TCT | CTG | ATC | GGC | GAG | TAC | TAT | GTA | GAA | GCT | 747 |
| Gly | Trp | Phe | Ser | Leu 190 | Gln | Ser | Leu | Ile | Gly 195 | Glu | Tyr | Tyr | Val | Glu 200 | Ala | |
| GGT | CAC | GGC | CCA | CTT | TCG | GAT | CTC | GCT | ATT | ACG | AAA | CTG | CCC | AAT | GAT | 795 |
| Gly 205 | His | Gly | Pro | Leu | Ser 210 | Asp | Leu | Ala | Ile | Thr 215 | Lys | Leu | Pro | Asn | Asp 220 | |
| GGT | AGC | TCT | AAT | TCG | AGC | GGT | CAT | GGA | ATG | GAA | GGA | GAT | CTT | CCT | GCC | 843 |
| Gly | Ser | Ser | Asn | Ser 225 | Ser | Gly | His | Gly | Met 230 | Glu | Gly | Asp | Leu | Pro 235 | Ala | |
| GCG | TGG | CGC | AAC | GCG | TTC | ACC | GCT | GCT | AAC | GCC | ACA | CCT | GAG | GGT | CGC | 891 |
| Ala | Trp | Arg | Asn | Ala 240 | Phe | Thr | Ala | Ala | Asn 245 | Ala | Thr | Pro | Glu | Gly 250 | Arg | |
| GCA | CGC | ATG | GCA | CTA | GCC | TTT | GCG | CTC | GGT | CAG | TGG | TCT | CCG | TGG | TTG | 939 |
| Ala | Arg | Met 255 | Ala | Leu | Ala | Phe | Ala 260 | Leu | Gly | Gln | Trp | Ser 265 | Pro | Trp | Leu | |
| GCC | GAC | AAC | ACG | CCC | CAA | CCT | GAT | CTC | GAT | GAT | CCT | GAG | GCC | ATC | GCG | 987 |
| Ala | Asp | Asn | Thr 270 | Pro | Gln | Pro | Asp | Leu 275 | Asp | Asp | Pro | Glu | Ala 280 | Ile | Ala | |
| GAT | TCC | GTA | TAT | GAG | TCT | GCC | ATG | CGA | CTT | GCA | GGA | AGC | CCT | GGG | GGA | 1035 |
| Asp 285 | Ser | Val | Tyr | Glu | Ser 290 | Ala | Met | Arg | Leu | Ala 295 | Gly | Ser | Pro | Gly | Gly 300 | |
| GAA | GCG | CGC | ATA | ATG | TTC | GAG | AAC | GCC | GCT | CGA | GGG | CAA | CAG | CTC | TCT | 1083 |
| Glu | Ala | Arg | Ile | Met 305 | Phe | Glu | Asn | Ala | Ala 310 | Arg | Gly | Gln | Gln | Leu 315 | Ser | |
| TGG | AAC | GAC | GAC | ATC | GAC | TAT | GCG | GAT | TTC | TGG | GAG | AAC | TCA | AAC | CCA | 1131 |
| Trp | Asn | Asp | Asp | Ile 320 | Asp | Tyr | Ala | Asp | Phe 325 | Trp | Glu | Asn | Ser | Asn 330 | Pro | |
| GCC | ATG | AAG | AGC | GCC | GTT | CAG | GAG | CTG | TAC | GAC | ACG | GCC | GGC | CTT | GAT | 1179 |
| Ala | Met | Lys | Ser 335 | Ala | Val | Gln | Glu | Leu 340 | Tyr | Asp | Thr | Ala | Gly 345 | Leu | Asp | |
| CTG | CAG | TCC | GAT | ATA | GAA | ACG | GTA | AAT | TCC | CAG | CCA | CGC | ATA | GAG | GCA | 1227 |
| Leu | Gln | Ser | Asp 350 | Ile | Glu | Thr | Val | Asn 355 | Ser | Gln | Pro | Arg | Ile 360 | Glu | Ala | |
| TCG | CAG | TAT | GCG | CTC | GAC | TAC | TGG | AAC | ACG | CCA | GGT | CGC | AAT | GTC | ATT | 1275 |
| Ser 365 | Gln | Tyr | Ala | Leu | Asp 370 | Tyr | Trp | Asn | Thr | Pro 375 | Gly | Arg | Asn | Val | Ile 380 | |
| GGC | GAC | CCC | GAA | GTT | CCT | GTG | CTG | CGC | CTG | CAT | ATG | ATA | GGC | GAC | TAC | 1323 |
| Gly | Asp | Pro | Glu | Val 385 | Pro | Val | Leu | Arg | Leu 390 | His | Met | Ile | Gly | Asp 395 | Tyr | |
| CAA | ATT | CCC | TAT | AGT | CTT | GTA | CAG | GGC | TAC | AGC | GAT | CTT | ATC | TCA | GAG | 1371 |
| Gln | Ile | Pro | Tyr | Ser 400 | Leu | Val | Gln | Gly | Tyr 405 | Ser | Asp | Leu | Ile | Ser 410 | Glu | |
| AAC | AAC | AAT | GAT | GAC | TTG | TAC | AGA | ACT | GCT | TTT | GTG | CAA | TCC | ACT | GGA | 1419 |
| Asn | Asn | Asn | Asp | Asp 415 | Leu | Tyr | Arg | Thr | Ala 420 | Phe | Val | Gln | Ser | Thr 425 | Gly | |
| CAC | TGC | AAT | TTC | ACA | GCT | GCA | GAA | AGT | TCC | GCT | GCG | ATT | GAG | GTC | ATG | 1467 |
| His | Cys | Asn 430 | Phe | Thr | Ala | Ala | Glu 435 | Ser | Ser | Ala | Ala | Ile 440 | Glu | Val | Met | |
| ATG | CAA | CGG | CTT | GAC | ACG | GGT | GAG | TGG | CCG | AGC | ACC | GAG | CCG | GAT | GAT | 1515 |
| Met | Gln | Arg | Leu | Asp 445 | Thr | Gly | Glu | Trp | Pro 450 | Ser | Thr | Glu | Pro | Asp 455 | Asp 460 | |

| | | | | | | | | | | | | | | | | |
|---|---|---|---|---|---|---|---|---|---|---|---|---|---|---|---|---|
| CTG | AAT | GCA | ATT | GCC | GAA | GCC | TCA | AAC | ACC | GGA | ACT | GAA | GCA | CGT | TTC | 1563 |
| Leu | Asn | Ala | Ile | Ala | Glu | Ala | Ser | Asn | Thr | Gly | Thr | Glu | Ala | Arg | Phe | |
| | | | 465 | | | | | 470 | | | | | 475 | | | |
| ATG | GCC | CTA | GAT | GGC | TGG | GAA | ATA | CCC | GAG | TAC | AAT | CGT | ACT | TGG | AAG | 1611 |
| Met | Ala | Leu | Asp | Gly | Trp | Glu | Ile | Pro | Glu | Tyr | Asn | Arg | Thr | Trp | Lys | |
| | | | 480 | | | | | 485 | | | | | 490 | | | |
| CCT | GAA | TAA | | | | | | | | | | | | | | 1620 |
| Pro | Glu | | | | | | | | | | | | | | | |

( 2 ) INFORMATION FOR SEQ ID NO:6:

( i ) SEQUENCE CHARACTERISTICS:
            ( A ) LENGTH: 3029 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: CDS
            ( B ) LOCATION: 136..1617

( x i ) SEQUENCE DESCRIPTION: SEQ ID NO:6:

| | | | | | |
|---|---|---|---|---|---|
| GGATCCTTAG | GAATCTAAAC | ATTCTGGTTG | ACACTCCACA | TTTTGAATGT | CAGCATTTCG | 60 |
| GCCATGGCTG | CTATGCAGCC | TGTTATTGCA | TTTGAAATGG | AATAGATCAG | CAAACTTATC | 120 |

| | | | | | | | | | | | | | | | | |
|---|---|---|---|---|---|---|---|---|---|---|---|---|---|---|---|---|
| GGGAGGATGA | GTATT | ATG | ATA | ATC | AAG | GGT | AGT | GTA | CCG | GGT | AAA | GCC | GGA | | | 171 |
| | | Met | Ile | Ile | Lys | Gly | Ser | Val | Pro | Gly | Lys | Ala | Gly | | | |
| | | 1 | | | 5 | | | | | 10 | | | | | | |
| GGA | AAA | CCT | CGA | GCG | ACC | ATC | TTT | CAT | AGT | TCT | ATT | GCA | ACG | CTA | CTT | 219 |
| Gly | Lys | Pro | Arg | Ala | Thr | Ile | Phe | His | Ser | Ser | Ile | Ala | Thr | Leu | Leu | |
| | | 15 | | | | 20 | | | | | 25 | | | | | |
| TTA | ACC | ACA | GTC | TCA | CTG | TCA | GGA | GTA | GCG | CCA | GCA | TTT | GCA | CAG | GCG | 267 |
| Leu | Thr | Thr | Val | Ser | Leu | Ser | Gly | Val | Ala | Pro | Ala | Phe | Ala | Gln | Ala | |
| | 30 | | | | | 35 | | | | | 40 | | | | | |
| CCG | TCT | GTG | CAC | CAA | CAC | GTC | GCC | TTC | ACT | GAG | GAA | ATT | GGA | GAC | CTT | 315 |
| Pro | Ser | Val | His | Gln | His | Val | Ala | Phe | Thr | Glu | Glu | Ile | Gly | Asp | Leu | |
| 45 | | | | 50 | | | | | 55 | | | | | 60 | | |
| CCC | GAC | GGC | TCA | AGT | TAC | ATG | ATC | CGT | GTG | CCG | GAG | AAC | TGG | AAC | GGC | 363 |
| Pro | Asp | Gly | Ser | Ser | Tyr | Met | Ile | Arg | Val | Pro | Glu | Asn | Trp | Asn | Gly | |
| | | | 65 | | | | | 70 | | | | | 75 | | | |
| GTG | TTA | ATT | CGC | GAC | CTA | GAC | CTT | GTC | AGC | GGC | ACC | AGC | AAT | TCT | AAC | 411 |
| Val | Leu | Ile | Arg | Asp | Leu | Asp | Leu | Val | Ser | Gly | Thr | Ser | Asn | Ser | Asn | |
| | | 80 | | | | | 85 | | | | | 90 | | | | |
| GCC | GCA | AGG | TAC | GAA | ACC | ATG | CTG | AAA | GAA | GGT | TTT | GCC | GTT | GCT | GGC | 459 |
| Ala | Ala | Arg | Tyr | Glu | Thr | Met | Leu | Lys | Glu | Gly | Phe | Ala | Val | Ala | Gly | |
| | | 95 | | | | 100 | | | | | 105 | | | | | |
| ACG | GCG | AGG | CAT | CCC | CTT | CGG | CAA | TGG | CAA | TAT | GAC | CCC | GCT | CAC | GAG | 507 |
| Thr | Ala | Arg | His | Pro | Leu | Arg | Gln | Trp | Gln | Tyr | Asp | Pro | Ala | His | Glu | |
| | 110 | | | | | 115 | | | | | 120 | | | | | |
| ATT | GAA | AAC | CTC | AAT | CAC | GTG | CTG | GAC | ACA | TTC | GAG | GAA | AAT | TAC | GGT | 555 |
| Ile | Glu | Asn | Leu | Asn | His | Val | Leu | Asp | Thr | Phe | Glu | Glu | Asn | Tyr | Gly | |
| 125 | | | | | 130 | | | | | 135 | | | | | 140 | |
| TCA | CCT | GAA | AGA | GTT | ATC | CAG | TAC | GGT | TGC | TCG | GGT | GGG | GCA | CAC | GTG | 603 |
| Ser | Pro | Glu | Arg | Val | Ile | Gln | Tyr | Gly | Cys | Ser | Gly | Gly | Ala | His | Val | |
| | | | | 145 | | | | | 150 | | | | | 155 | | |
| TCA | CTA | GCC | GTG | GCA | GAG | GAC | TTC | TCG | GAC | CGC | GTA | GAT | GGC | TCA | GTT | 651 |
| Ser | Leu | Ala | Val | Ala | Glu | Asp | Phe | Ser | Asp | Arg | Val | Asp | Gly | Ser | Val | |
| | | | 160 | | | | | 165 | | | | | 170 | | | |
| GCT | CTA | GCT | GCT | CAT | ACT | CCT | GTC | TGG | ATA | ATG | AAT | TCT | TTC | TTG | GAC | 699 |
| Ala | Leu | Ala | Ala | His | Thr | Pro | Val | Trp | Ile | Met | Asn | Ser | Phe | Leu | Asp | |
| | | 175 | | | | | 180 | | | | | 185 | | | | |
| GGA | TGG | TTT | TCG | CTG | CAG | TCT | CTG | ATC | GGC | GAG | TAC | TAT | GTA | GAA | GCT | 747 |
| Gly | Trp | Phe | Ser | Leu | Gln | Ser | Leu | Ile | Gly | Glu | Tyr | Tyr | Val | Glu | Ala | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 190 |     |     |     |     | 195 |     |     |     |     | 200 |     |      |
| GGT | CAC | GGC | CCA | CTT | TCG | GAT | CTC | GCT | ATT | ACG | AAA | CTG | CCC | AAT | GAT | 795  |
| Gly | His | Gly | Pro | Leu | Ser | Asp | Leu | Ala | Ile | Thr | Lys | Leu | Pro | Asn | Asp |      |
| 205 |     |     |     |     | 210 |     |     |     |     | 215 |     |     |     |     | 220 |      |
| GGT | AGC | TCT | AAT | TCG | AGC | GGT | CAT | GGA | ATG | GAA | GGA | GAT | CTT | CCT | GCC | 843  |
| Gly | Ser | Ser | Asn | Ser | Ser | Gly | His | Gly | Met | Glu | Gly | Asp | Leu | Pro | Ala |      |
|     |     |     |     | 225 |     |     |     |     | 230 |     |     |     |     | 235 |     |      |
| GCG | TGG | CGC | AAC | GCG | TTC | ACC | GCT | GCT | AAC | GCC | ACA | CCT | GAG | GGT | CGC | 891  |
| Ala | Trp | Arg | Asn | Ala | Phe | Thr | Ala | Ala | Asn | Ala | Thr | Pro | Glu | Gly | Arg |      |
|     |     |     | 240 |     |     |     |     | 245 |     |     |     |     | 250 |     |     |      |
| GCA | CGC | ATG | GCA | CTA | GCC | TTT | GCG | CTC | GGT | CAG | TGG | TCT | CCG | TGG | TTG | 939  |
| Ala | Arg | Met | Ala | Leu | Ala | Phe | Ala | Leu | Gly | Gln | Trp | Ser | Pro | Trp | Leu |      |
|     |     | 255 |     |     |     |     | 260 |     |     |     |     | 265 |     |     |     |      |
| GCC | GAC | AAC | ACG | CCC | CAA | CCT | GAT | CTC | GAT | GAT | CCT | GAG | GCC | ATC | GCG | 987  |
| Ala | Asp | Asn | Thr | Pro | Gln | Pro | Asp | Leu | Asp | Asp | Pro | Glu | Ala | Ile | Ala |      |
|     |     | 270 |     |     |     |     | 275 |     |     |     |     | 280 |     |     |     |      |
| GAT | TCC | GTA | TAT | GAG | TCT | GCC | ATG | CGA | CTT | GCA | GGA | AGC | CCT | GGG | GGA | 1035 |
| Asp | Ser | Val | Tyr | Glu | Ser | Ala | Met | Arg | Leu | Ala | Gly | Ser | Pro | Gly | Gly |      |
| 285 |     |     |     |     | 290 |     |     |     |     | 295 |     |     |     |     | 300 |      |
| GAA | GCG | CGC | ATA | ATG | TTC | GAG | AAC | GCC | GCT | CGA | GGG | CAA | CAG | CTC | TCT | 1083 |
| Glu | Ala | Arg | Ile | Met | Phe | Glu | Asn | Ala | Ala | Arg | Gly | Gln | Gln | Leu | Ser |      |
|     |     |     |     | 305 |     |     |     |     | 310 |     |     |     |     | 315 |     |      |
| TGG | AAC | GAC | GAC | ATC | GAC | TAT | GCG | GAT | TTC | TGG | GAG | AAC | TCA | AAC | CCA | 1131 |
| Trp | Asn | Asp | Asp | Ile | Asp | Tyr | Ala | Asp | Phe | Trp | Glu | Asn | Ser | Asn | Pro |      |
|     |     |     | 320 |     |     |     |     | 325 |     |     |     |     | 330 |     |     |      |
| GCC | ATG | AAG | AGC | GCC | GTT | CAG | GAG | CTG | TAC | GAC | ACG | GCC | GGC | CTT | GAT | 1179 |
| Ala | Met | Lys | Ser | Ala | Val | Gln | Glu | Leu | Tyr | Asp | Thr | Ala | Gly | Leu | Asp |      |
|     |     | 335 |     |     |     |     | 340 |     |     |     |     | 345 |     |     |     |      |
| CTG | CAG | TCC | GAT | ATA | GAA | ACG | GTA | AAT | TCC | CAG | CCA | CGC | ATA | GAG | GCA | 1227 |
| Leu | Gln | Ser | Asp | Ile | Glu | Thr | Val | Asn | Ser | Gln | Pro | Arg | Ile | Glu | Ala |      |
|     | 350 |     |     |     |     | 355 |     |     |     |     | 360 |     |     |     |     |      |
| TCG | CAG | TAT | GCG | CTC | GAC | TAC | TGG | AAC | ACG | CCA | GGT | CGC | AAT | GTC | ATT | 1275 |
| Ser | Gln | Tyr | Ala | Leu | Asp | Tyr | Trp | Asn | Thr | Pro | Gly | Arg | Asn | Val | Ile |      |
| 365 |     |     |     |     | 370 |     |     |     |     | 375 |     |     |     |     | 380 |      |
| GGC | GAC | CCC | GAA | GTT | CCT | GTG | CTG | CGC | CTG | CAT | ATG | ATA | GGC | GAC | TAC | 1323 |
| Gly | Asp | Pro | Glu | Val | Pro | Val | Leu | Arg | Leu | His | Met | Ile | Gly | Asp | Tyr |      |
|     |     |     |     | 385 |     |     |     |     | 390 |     |     |     |     | 395 |     |      |
| CAA | ATT | CCC | TAT | AGT | CTT | GTA | CAG | GGC | TAC | AGC | GAT | CTT | ATC | TCA | GAG | 1371 |
| Gln | Ile | Pro | Tyr | Ser | Leu | Val | Gln | Gly | Tyr | Ser | Asp | Leu | Ile | Ser | Glu |      |
|     |     |     | 400 |     |     |     |     | 405 |     |     |     |     | 410 |     |     |      |
| AAC | AAC | AAT | GAT | GAC | TTG | TAC | AGA | ACT | GCT | TTT | GTG | CAA | TCC | ACT | GGA | 1419 |
| Asn | Asn | Asn | Asp | Asp | Leu | Tyr | Arg | Thr | Ala | Phe | Val | Gln | Ser | Thr | Gly |      |
|     |     | 415 |     |     |     |     | 420 |     |     |     |     | 425 |     |     |     |      |
| CAC | TGC | AAT | TTC | ACA | GCT | GCA | GAA | AGT | TCC | GCT | GCG | ATT | GAG | GTC | ATG | 1467 |
| His | Cys | Asn | Phe | Thr | Ala | Ala | Glu | Ser | Ser | Ala | Ala | Ile | Glu | Val | Met |      |
|     | 430 |     |     |     |     | 435 |     |     |     |     | 440 |     |     |     |     |      |
| ATG | CAA | CGG | CTT | GAC | ACG | GGT | GAG | TGG | CCG | AGC | ACC | GAG | CCG | GAT | GAT | 1515 |
| Met | Gln | Arg | Leu | Asp | Thr | Gly | Glu | Trp | Pro | Ser | Thr | Glu | Pro | Asp | Asp |      |
| 445 |     |     |     |     | 450 |     |     |     |     | 455 |     |     |     |     | 460 |      |
| CTG | AAT | GCA | ATT | GCC | GAA | GCC | TCA | AAC | ACC | GGA | ACT | GAA | GCA | CGT | TTC | 1563 |
| Leu | Asn | Ala | Ile | Ala | Glu | Ala | Ser | Asn | Thr | Gly | Thr | Glu | Ala | Arg | Phe |      |
|     |     |     |     | 465 |     |     |     |     | 470 |     |     |     |     | 475 |     |      |
| ATG | GCC | CTA | GAT | GGC | TGG | GAA | ATA | CCC | GAG | TAC | AAT | CGT | ACT | TGG | AAG | 1611 |
| Met | Ala | Leu | Asp | Gly | Trp | Glu | Ile | Pro | Glu | Tyr | Asn | Arg | Thr | Trp | Lys |      |
|     |     |     | 480 |     |     |     |     | 485 |     |     |     |     | 490 |     |     |      |
| CCT | GAA | TAATCACCAT | TCTGGAGGCT | CACGTTCGCG | AAGGGTTGCG | GCGAAGAAAA | | | | | | | | | | 1667 |
| Pro | Glu |            |            |            |            |            | | | | | | | | | |      |
| CATGCGCCGC | AACCTATCCT | CCAAACAAGG | GCCAGTTCAA | CGACGAACAA | GCCAGACCGG | | | | | | | | | | | 1727 |
| CGCAAGCCGC | GCTAATCTAA | TTCACCGCTC | CAACCCGCGA | TCTCGCGACC | GCCCGCGCTG | | | | | | | | | | | 1787 |
| CATGTCGAGC | TTCTGTTGCT | GCGCCCGCTC | AAGCGTATAA | TCACGCCGGA | TAATCGTTTC | | | | | | | | | | | 1847 |

```
CCGCGCTTTG TTCGTGATCC TTGCAACGTC CTTGATGCGA TCGACGTTAC GGGCTGTCTC    1907

TGAAGGCTGT GAGCGTGTGC GATCAAGCGC CTGATCGATA TCGCGATGAT TGCTTGATCC    1967

GAACCGGATC TGCATAGCCC GGGCAATACG TTTGGCTTCA TCAAGCGCCT GTTTGCCATC    2027

AGCCGTCTTT TCGAGCTGAT CGACAAAGCC CGTCCGTGCC TTCGCATCCT TGATCTGATC    2087

GAGCTGCCTG AGCAGGGTTT CGCTGCGAGG TGAGAGGCCA GGAATCTCGA CGCGATCATT    2147

ATTGTCACGC CGCCATTGTT CGGCTTCCTT TTCCTCGGCA AAGCGCCGCG TCCAGGTCTT    2207

CCCCGCCGCG TCCAGATGCG AACTCATCGC CTCGGCCCGC TTGAGGGCAT TTTTTGCGCT    2267

CGGCATTGGC ACCGAACAGG CCGAACTTGC CGCGCAGCTG TTGATTTCTG CTGAGAAGTG    2327

ACCCGGTATT GGAGTGAACC CCTGGGACTG GACCAGCGGG AAGAAAAGC TGATACGCTC     2387

TGTGGGCCTT GAATGGAGAA GGTCCATGTC ACCAAGAGGT CCCTACCGCC GTCACTCGAT    2447

GCAGTTCAAG CGTAAGCGCC AAGCCTGGCC CGTCTGGTGA TGGCTGCCTT TGAGCGCTAT    2507

CGACACCCCG GAGTTAGTGA TGGGTGTCAT GTTCTATGTC TGCGACTATG CCTGCAGATA    2567

GAAGTTTCCA GTTGATCGAG GCGGTTCCGG ATCGGATGGA GGGCGCTCCG GTTGCGCGGC    2627

GACGCCGGTG GTCGGACGCG TTCAAGGCCG AGATGGTAGC GCGCAGCTTC GAACCTGGAA    2687

CGAATGTGTC GGCACTGGCG CGCGAGATCG GCATCCAGTC CTCGCAGTTG TTCGGCTGGC    2747

GCGCCGAGGC CCTCAAGCGC GGAGAGGTGG AAAGGCGCGA TGTTGATATC GTTGCAACGC    2807

AAGCCTCTCG CTTGGTGAGC GGGACGGTCG AGATCGCGGT CAACGACACG GTGATCCGGG    2867

TCGGCATTGA TATCGGGGAA GACCATTTGC GGCGCGTGAT CCGCGCTGTG CGGTCGGCAT    2927

GATCCCTGCG GGTGTGAAGG TCTATCTGGC CAGCCAGCCG GTAGACTTCA GGAAAGGTCC    2987

AGACGGCCTT GTTGGCCTGG TGCGCGATGC TGGAGCGGAT CC                      3029
```

( 2 ) INFORMATION FOR SEQ ID NO:7:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GGATCCTTAG GAATCTAAAC ATTCTGGTTG ACACTCCACA TTTTGAATGT CAGCATTTCG     60

GCCATGGCTG CTATGCAGCC TGTTATTGCA TTTGAAATGG AATAGATCAG CAAACTTATC    120

GGGAGGATGA GTATT                                                    135
```

( 2 ) INFORMATION FOR SEQ ID NO:8:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..126

( x i ) SEQUENCE DESCRIPTION: SEQ ID NO:8:

```
ATG ATA ATC AAG GGT AGT GTA CCG GGT AAA GCC GGA GGA AAA CCT CGA      48
Met Ile Ile Lys Gly Ser Val Pro Gly Lys Ala Gly Gly Lys Pro Arg
 1               5                  10                 15

GCG ACC ATC TTT CAT AGT TCT ATT GCA ACG CTA CTT TTA ACC ACA GTC      96
```

```
Ala  Thr  Ile  Phe  His  Ser  Ser  Ile  Ala  Thr  Leu  Leu  Leu  Thr  Thr  Val
          20                      25                      30

TCA  CTG  TCA  GGA  GTA  GCG  CCA  GCA  TTT  GCA                              126
Ser  Leu  Ser  Gly  Val  Ala  Pro  Ala  Phe  Ala
          35                      40
```

( 2 ) INFORMATION FOR SEQ ID NO:9:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Ile  Ile  Lys  Gly  Ser  Val  Pro  Gly  Lys  Ala  Gly  Gly  Lys  Pro  Arg
 1                  5                       10                      15

Ala  Thr  Ile  Phe  His  Ser  Ser  Ile  Ala  Thr  Leu  Leu  Leu  Thr  Thr  Val
          20                      25                      30

Ser  Leu  Ser  Gly  Val  Ala  Pro  Ala  Phe  Ala
          35                      40
```

( 2 ) INFORMATION FOR SEQ ID NO:10:

( i ) SEQUENCE CHARACTERISTICS:
        ( A ) LENGTH: 1409 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
TCACCATTCT  GGAGGCTCAC  GTTCGCGAAG  GGTTGCGGCG  AAGAAAACAT  GCGCCGCAAC     60
CTATCCTCCA  AACAAGGGCC  AGTTCAACGA  CGAACAAGCC  AGACCGGCGC  AAGCCGCGCT    120
AATCTAATTC  ACCGCTCCAA  CCCGCGATCT  CGCGACCGCC  CGCGCTGCAT  GTCGAGCTTC    180
TGTTGCTGCG  CCCGCTCAAG  CGTATAATCA  CGCCGGATAA  TCGTTTCCCG  CGCTTTGTTC    240
GTGATCCTTG  CAACGTCCTT  GATGCGATCG  ACGTTACGGG  CTGTCTCTGA  AGGCTGTGAG    300
CGTGTGCGAT  CAAGCGCCTG  ATCGATATCG  CGATGATTGC  TTGATCCGAA  CCGGATCTGC    360
ATAGCCCGGG  CAATACGTTT  GGCTTCATCA  AGCGCCTGTT  TGCCATCAGC  CGTCTTTTCG    420
AGCTGATCGA  CAAAGCCCGT  CCGTGCCTTC  GCATCCTTGA  TCTGATCGAG  CTGCCTGAGC    480
AGGGTTTCGC  TGCGAGGTGA  GAGGCCAGGA  ATCTCGACGC  GATCATTATT  GTCACGCCGC    540
CATTGTTCGG  CTTCCTTTTC  CTCGGCAAAG  CGCCGCGTCC  AGGTCTTCCC  CGCCGCGTCC    600
AGATGCGAAC  TCATCGCCTC  GGCCCGCTTG  AGGGCATTTT  TTGCGCTCGG  CATTGGCACC    660
GAACAGGCCG  AACTTGCCGC  GCAGCTGTTG  ATTTCTGCTG  AGAAGTGACC  CGGTATTGGA    720
GTGAACCCCT  GGGACTGGAC  CAGCGGGGAA  GAAAAGCTGA  TACGCTCTGT  GGGCCTTGAA    780
TGGAGAAGGT  CCATGTCACC  AAGAGGTCCC  TACCGCCGTC  ACTCGATGCA  GTTCAAGCGT    840
AAGCGCCAAG  CCTGGCCCGT  CTGGTGATGG  CTGCCTTTGA  GCGCTATCGA  CACCCCGGAG    900
TTAGTGATGG  GTGTCATGTT  CTATGTCTGC  GACTATGCCT  GCAGATAGAA  GTTTCCAGTT    960
GATCGAGGCG  GTTCCGGATC  GGATGGAGGG  CGCTCCGGTT  GCGCGGCGAC  GCCGGTGGTC   1020
GGACGCGTTC  AAGGCCGAGA  TGGTAGCGCG  CAGCTTCGAA  CCTGGAACGA  ATGTGTCGGC   1080
ACTGGCGCGC  GAGATCGGCA  TCCAGTCCTC  GCAGTTGTTC  GGCTGGCGCG  CCGAGGCCCT   1140
CAAGCGCGGA  GAGGTGGAAA  GGCGCGATGT  TGATATCGTT  GCAACGCAAG  CCTCTCGCTT   1200
GGTGAGCGGG  ACGGTCGAGA  TCGCGGTCAA  CGACACGGTG  ATCCGGGTCG  GCATTGATAT   1260
```

```
CGGGGAAGAC CATTTGCGGC GCGTGATCCG CGCTGTGCGG TCGGCATGAT CCCTGCGGGT        1320

GTGAAGGTCT ATCTGGCCAG CCAGCCGGTA GACTTCAGGA AAGGTCCAGA CGGCCTTGTT        1380

GGCCTGGTGC GCGATGCTGG AGCGGATCC                                          1409
```

( 2 ) INFORMATION FOR SEQ ID NO:11:

( i ) SEQUENCE CHARACTERISTICS:
        ( A ) LENGTH: 1362 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1359

( x i ) SEQUENCE DESCRIPTION: SEQ ID NO:11:

```
ATG CAG GCG CCG TCT GTG CAC CAA CAC GTC GCC TTC ACT GAG GAA ATT          48
Met Gln Ala Pro Ser Val His Gln His Val Ala Phe Thr Glu Glu Ile
 1               5                  10                  15

GGA GAC CTT CCC GAC GGC TCA AGT TAC ATG ATC CGT GTG CCG GAG AAC          96
Gly Asp Leu Pro Asp Gly Ser Ser Tyr Met Ile Arg Val Pro Glu Asn
            20                  25                  30

TGG AAC GGC GTG TTA ATT CGC GAC CTA GAC CTT GTC AGC GGC ACC AGC         144
Trp Asn Gly Val Leu Ile Arg Asp Leu Asp Leu Val Ser Gly Thr Ser
        35                  40                  45

AAT TCT AAC GCC GCA AGG TAC GAA ACC ATG CTG AAA GAA GGT TTT GCC         192
Asn Ser Asn Ala Ala Arg Tyr Glu Thr Met Leu Lys Glu Gly Phe Ala
     50                  55                  60

GTT GCT GGC ACG GCG AGG CAT CCC CTT CGG CAA TGG CAA TAT GAC CCC         240
Val Ala Gly Thr Ala Arg His Pro Leu Arg Gln Trp Gln Tyr Asp Pro
 65                  70                  75                  80

GCT CAC GAG ATT GAA AAC CTC AAT CAC GTG CTG GAC ACA TTC GAG GAA         288
Ala His Glu Ile Glu Asn Leu Asn His Val Leu Asp Thr Phe Glu Glu
                 85                  90                  95

AAT TAC GGT TCA CCT GAA AGA GTT ATC CAG TAC GGT TGC TCG GGT GGG         336
Asn Tyr Gly Ser Pro Glu Arg Val Ile Gln Tyr Gly Cys Ser Gly Gly
            100                 105                 110

GCA CAC GTG TCA CTA GCC GTG GCA GAG GAC TTC TCG GAC CGC GTA GAT         384
Ala His Val Ser Leu Ala Val Ala Glu Asp Phe Ser Asp Arg Val Asp
        115                 120                 125

GGC TCA GTT GCT CTA GCT GCT CAT ACT CCT GTC TGG ATA ATG AAT TCT         432
Gly Ser Val Ala Leu Ala Ala His Thr Pro Val Trp Ile Met Asn Ser
    130                 135                 140

TTC TTG GAC GGA TGG TTT TCG CTG CAG TCT CTG ATC GGC GAG TAC TAT         480
Phe Leu Asp Gly Trp Phe Ser Leu Gln Ser Leu Ile Gly Glu Tyr Tyr
145                 150                 155                 160

GTA GAA GCT GGT CAC GGC CCA CTT TCG GAT CTC GCT ATT ACG AAA CTG         528
Val Glu Ala Gly His Gly Pro Leu Ser Asp Leu Ala Ile Thr Lys Leu
                165                 170                 175

CCC AAT GAT GGT AGC TCT AAT TCG AGC GGT CAT GGA ATG GAA GGA GAT         576
Pro Asn Asp Gly Ser Ser Asn Ser Ser Gly His Gly Met Glu Gly Asp
            180                 185                 190

CTT CCT GCC GCG TGG CGC AAC GCG TTC ACC GCT GCT AAC GCC ACA CCT         624
Leu Pro Ala Ala Trp Arg Asn Ala Phe Thr Ala Ala Asn Ala Thr Pro
        195                 200                 205

GAG GGT CGC GCA CGC ATG GCA CTA GCC TTT GCG CTC GGT CAG TGG TCT         672
Glu Gly Arg Ala Arg Met Ala Leu Ala Phe Ala Leu Gly Gln Trp Ser
    210                 215                 220

CCG TGG TTG GCC GAC AAC ACG CCC CAA CCT GAT CTC GAT GAT CCT GAG         720
Pro Trp Leu Ala Asp Asn Thr Pro Gln Pro Asp Leu Asp Asp Pro Glu
```

| | | | | | | | | | | | | | | | |
|---|---|---|---|---|---|---|---|---|---|---|---|---|---|---|---|
| 225 | | | | | 230 | | | | | 235 | | | | | 240 |
| GCC | ATC | GCG | GAT | TCC | GTA | TAT | GAG | TCT | GCC | ATG | CGA | CTT | GCA | GGA | AGC | 768
| Ala | Ile | Ala | Asp | Ser | Val | Tyr | Glu | Ser | Ala | Met | Arg | Leu | Ala | Gly | Ser |
| | | | | 245 | | | | | 250 | | | | | 255 | |

225 230 235 240

GCC ATC GCG GAT TCC GTA TAT GAG TCT GCC ATG CGA CTT GCA GGA AGC 768
Ala Ile Ala Asp Ser Val Tyr Glu Ser Ala Met Arg Leu Ala Gly Ser
                245                 250                 255

CCT GGG GGA GAA GCG CGC ATA ATG TTC GAG AAC GCC GCT CGA GGG CAA 816
Pro Gly Gly Glu Ala Arg Ile Met Phe Glu Asn Ala Ala Arg Gly Gln
            260                 265                 270

CAG CTC TCT TGG AAC GAC GAC ATC GAC TAT GCG GAT TTC TGG GAG AAC 864
Gln Leu Ser Trp Asn Asp Asp Ile Asp Tyr Ala Asp Phe Trp Glu Asn
        275                 280                 285

TCA AAC CCA GCC ATG AAG AGC GCC GTT CAG GAG CTG TAC GAC ACG GCC 912
Ser Asn Pro Ala Met Lys Ser Ala Val Gln Glu Leu Tyr Asp Thr Ala
    290                 295                 300

GGC CTT GAT CTG CAG TCC GAT ATA GAA ACG GTA AAT TCC CAG CCA CGC 960
Gly Leu Asp Leu Gln Ser Asp Ile Glu Thr Val Asn Ser Gln Pro Arg
305                 310                 315                 320

ATA GAG GCA TCG CAG TAT GCG CTC GAC TAC TGG AAC ACG CCA GGT CGC 1008
Ile Glu Ala Ser Gln Tyr Ala Leu Asp Tyr Trp Asn Thr Pro Gly Arg
                325                 330                 335

AAT GTC ATT GGC GAC CCC GAA GTT CCT GTG CTG CGC CTG CAT ATG ATA 1056
Asn Val Ile Gly Asp Pro Glu Val Pro Val Leu Arg Leu His Met Ile
            340                 345                 350

GGC GAC TAC CAA ATT CCC TAT AGT CTT GTA CAG GGC TAC AGC GAT CTT 1104
Gly Asp Tyr Gln Ile Pro Tyr Ser Leu Val Gln Gly Tyr Ser Asp Leu
        355                 360                 365

ATC TCA GAG AAC AAC AAT GAT GAC TTG TAC AGA ACT GCT TTT GTG CAA 1152
Ile Ser Glu Asn Asn Asn Asp Asp Leu Tyr Arg Thr Ala Phe Val Gln
    370                 375                 380

TCC ACT GGA CAC TGC AAT TTC ACA GCT GCA GAA AGT TCC GCT GCG ATT 1200
Ser Thr Gly His Cys Asn Phe Thr Ala Ala Glu Ser Ser Ala Ala Ile
385                 390                 395                 400

GAG GTC ATG ATG CAA CGG CTT GAC ACG GGT GAG TGG CCG AGC ACC GAG 1248
Glu Val Met Met Gln Arg Leu Asp Thr Gly Glu Trp Pro Ser Thr Glu
                405                 410                 415

CCG GAT GAT CTG AAT GCA ATT GCC GAA GCC TCA AAC ACC GGA ACT GAA 1296
Pro Asp Asp Leu Asn Ala Ile Ala Glu Ala Ser Asn Thr Gly Thr Glu
            420                 425                 430

GCA CGT TTC ATG GCC CTA GAT GGC TGG GAA ATA CCC GAG TAC AAT CGT 1344
Ala Arg Phe Met Ala Leu Asp Gly Trp Glu Ile Pro Glu Tyr Asn Arg
        435                 440                 445

ACT TGG AAG CCT GAA TAA                                          1362
Thr Trp Lys Pro Glu
    450

( 2 ) INFORMATION FOR SEQ ID NO:12:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Met Gln Ala Pro Ser Val His Gln His Val Ala Phe Thr Glu Glu Ile
 1               5                  10                  15

Gly Asp Leu Pro Asp Gly Ser Ser Tyr Met Ile Arg Val Pro Glu Asn
                20                  25                  30

Trp Asn Gly Val Leu Ile Arg Asp Leu Asp Leu Val Ser Gly Thr Ser
            35                  40                  45

Asn Ser Asn Ala Ala Arg Tyr Glu Thr Met Leu Lys Glu Gly Phe Ala
        50                  55                  60

```
Val Ala Gly Thr Ala Arg His Pro Leu Arg Gln Trp Gln Tyr Asp Pro
 65              70              75              80

Ala His Glu Ile Glu Asn Leu Asn His Val Leu Asp Thr Phe Glu Glu
             85              90              95

Asn Tyr Gly Ser Pro Glu Arg Val Ile Gln Tyr Gly Cys Ser Gly Gly
            100             105             110

Ala His Val Ser Leu Ala Val Ala Glu Asp Phe Ser Asp Arg Val Asp
            115             120             125

Gly Ser Val Ala Leu Ala Ala His Thr Pro Val Trp Ile Met Asn Ser
            130             135             140

Phe Leu Asp Gly Trp Phe Ser Leu Gln Ser Leu Ile Gly Glu Tyr Tyr
145             150             155                         160

Val Glu Ala Gly His Gly Pro Leu Ser Asp Leu Ala Ile Thr Lys Leu
            165             170             175

Pro Asn Asp Gly Ser Ser Asn Ser Ser Gly His Gly Met Glu Gly Asp
            180             185             190

Leu Pro Ala Ala Trp Arg Asn Ala Phe Thr Ala Ala Asn Ala Thr Pro
            195             200             205

Glu Gly Arg Ala Arg Met Ala Leu Ala Phe Ala Leu Gly Gln Trp Ser
            210             215             220

Pro Trp Leu Ala Asp Asn Thr Pro Gln Pro Asp Leu Asp Asp Pro Glu
225             230             235             240

Ala Ile Ala Asp Ser Val Tyr Glu Ser Ala Met Arg Leu Ala Gly Ser
            245             250             255

Pro Gly Gly Glu Ala Arg Ile Met Phe Glu Asn Ala Ala Arg Gly Gln
            260             265             270

Gln Leu Ser Trp Asn Asp Asp Ile Asp Tyr Ala Asp Phe Trp Glu Asn
            275             280             285

Ser Asn Pro Ala Met Lys Ser Ala Val Gln Glu Leu Tyr Asp Thr Ala
            290             295             300

Gly Leu Asp Leu Gln Ser Asp Ile Glu Thr Val Asn Ser Gln Pro Arg
305             310             315             320

Ile Glu Ala Ser Gln Tyr Ala Leu Asp Tyr Trp Asn Thr Pro Gly Arg
            325             330             335

Asn Val Ile Gly Asp Pro Glu Val Pro Val Leu Arg Leu His Met Ile
            340             345             350

Gly Asp Tyr Gln Ile Pro Tyr Ser Leu Val Gln Gly Tyr Ser Asp Leu
            355             360             365

Ile Ser Glu Asn Asn Asp Leu Tyr Arg Thr Ala Phe Val Gln
            370             375             380

Ser Thr Gly His Cys Asn Phe Thr Ala Ala Glu Ser Ser Ala Ala Ile
385             390             395             400

Glu Val Met Met Gln Arg Leu Asp Thr Gly Glu Trp Pro Ser Thr Glu
            405             410             415

Pro Asp Asp Leu Asn Ala Ile Ala Glu Ala Ser Asn Thr Gly Thr Glu
            420             425             430

Ala Arg Phe Met Ala Leu Asp Gly Trp Glu Ile Pro Glu Tyr Asn Arg
            435             440             445

Thr Trp Lys Pro Glu
450
```

GENES ENCODING AND METHOD OF EXPRESSING AN ENZYME: PHTHALYL AMIDASE

BACKGROUND OF THE INVENTION

The present invention relates to the discovery of a specific enzyme that has not been previously described, a phthalyl amidase, which readily removes the phthalyl moiety from phthalyl-containing amides. The present invention also relates to an organism isolated from natural sources that produces the enzyme, DNA compounds that encode the enzyme, and methods for producing and using the enzyme.

The phthalimido functional group is an important tool in organic synthesis because of the protection it provides against unwanted reactions. However, dephthalylation reactions generally require harsh conditions and often have low yields thereby limiting the situations in which phthalimido protection can be employed.

Removal of a phthalyl protecting group from a phthalyl amide can be accomplished chemically, Kukolja et al., Croatica Chemica Acta 49:779, 1977, but yields are variable especially with substrates that are unstable to harsh reaction conditions.

Certain enzymes have previously been found that could be used to remove benzoyl groups from benzoylated amino acids. Toyoura et al., Chem. Pharm. Bull. 7:789, 1959. These enzymes were specific for benzoyl groups and for the amino acid to which they were attached. Others have also reported enzymes that will hydrolyze phthalate esters. Kurane et al., Agric. Biol. Chem. 44:529, 1980. However, none of these enzymes have been shown to operate on phthalyl amides.

In contrast, the phthalyl amidase enzyme of this invention catalyzes removal of the phthalyl group from a wide variety of phthalyl-containing compounds with improved yields over processes known in the art, exhibits stereochemical selectivity, and eliminates the need for harsh conditions to remove the protecting group.

SUMMARY OF THE INVENTION

The present invention provides a recombinant phthalyl amidase enzyme, which catalyzes the following type of reaction:

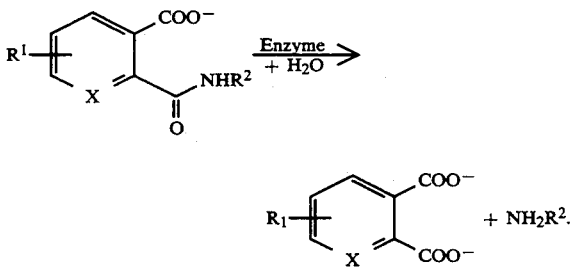

The present invention also provides DNA compounds that comprise isolated nucleotide sequences encoding the phthalyl amidase enzyme and methods for expressing such compounds. The present invention also provides recombinant DNA vectors encoding phthalyl amidase and host cells transformed with these DNA vectors. Preferred DNA compounds comprise an isolated nucleotide sequence encoding SEQ ID NO:2, especially SEQ ID NO:1 isolated from *Xanthobacter agilis*. Other preferred compounds of the present invention include DNA compounds that comprise isolated DNA sequences encoding the proenzyme form of phthalyl amidase enzyme (SEQ ID NO:4), including SEQ ID NO:3, SEQ ID NO:5, and the phthalyl amidase gene of *Xanthobacter agilis* (SEQ ID NO:6). DNA compounds of the current invention include recombinant DNA vectors, including expression vectors, which may be used to transform host cells.

The present invention also provides for DNA sequences of the naturally-occurring phthalyl amidase gene that control transcription, translation, and extra-cellular secretion of proteins. Thus, the present invention includes SEQ ID NO:7, SEQ ID NO:8, and SEQ ID NO:10.

Definitions:

Coding sequence—the sequence of DNA in the open reading frame of a gene that encodes the amino acid residue sequence of the protein expressed from the gene.

Gene—a segment of DNA that comprises a promoter, translational activating sequence, coding sequence, and 3' regulatory sequences, positioned to drive expression of the gene product.

Promoter—a DNA sequence that directs or initiates the transcription of DNA.

Recombinant DNA vector—any autonomously replicating or integrating DNA agent, including but not limited to plasmids, comprising a promoter and other regulatory sequences positioned to drive expression of a DNA sequence that encodes a polypeptide or RNA.

Recombinant DNA sequence—any DNA sequence, excluding the host chromosome from which the DNA is derived, which comprises a DNA sequence that has been isolated, synthesized, or partially synthesized.

Restriction fragment—any linear DNA molecule generated by the action of one or more restriction enzymes.

Translation activating sequence—a regulatory DNA sequence that, when transcribed into mRNA, promotes translation of mRNA into protein.

All nucleotide and amino acid abbreviations used in this disclosure are those accepted by the United States Patent and Trademark Office as set forth in 37 C.F.R. §1.822(b) (1993).

BRIEF DESCRIPTION OF THE FIGURES

The restriction enzyme and function maps presented in the drawings are approximate representations of the recombinant DNA vectors discussed herein. The restriction site information is not exhaustive. There may be more restriction enzymes sites of a given type than are actually shown on the map.

DETAILED DESCRIPTION OF THE INVENTION

Figure 1:
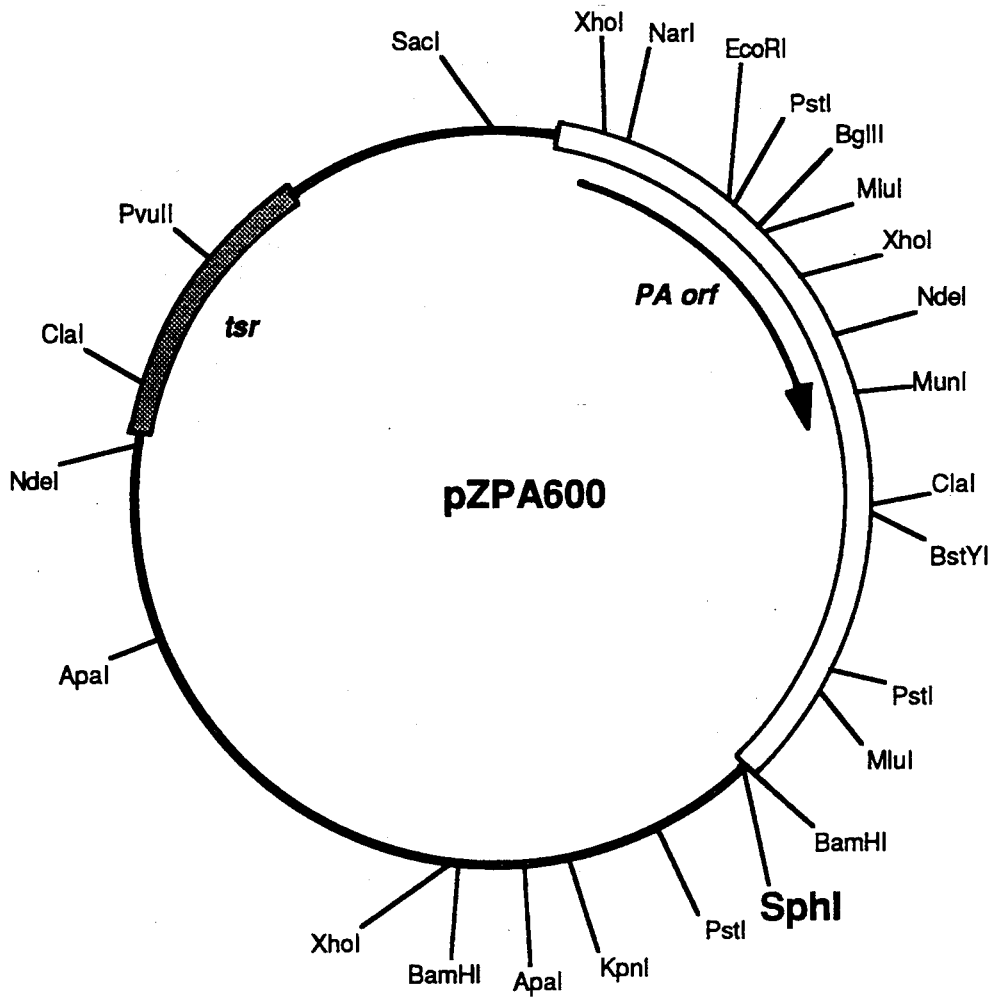
FIG. 1 is a restriction enzyme site and function map of plasmid pZPA600.

During the course of developing a chiral, shorter, and more efficient synthetic route to loracarbef ([6R-(6A,7B(R))]-7-[(aminophenylacetyl)amino]-3-chloro-8-oxo-azabicyclo[4,2,0]oct-2-ene-2-carboxylic acid), the Mitsunobu reaction (see e.g. Hughes, D. L. Organic reactions 42:336, 1992; Bose, A. K. et al., Can. J. Chem. 62:2498, 1984) was selected for forming the beta-lactam ring from a chiral linear amino acid ester intermediate.

Several reactants with one N-valence protected and a few reactants with both N-valences protected were examined in Mitsunobu reactions. They were either not cyclized or were cyclized in poor yield.

It was discovered that problems in forming the beta-lactam ring via Mitsunobu reactions could be overcome if both valences of the Q-nitrogen of the chiral linear amino acid ester intermediate were protected with a phthalimido group. However, no known chemical reaction was available to remove the phthalimido moiety and regenerate free amine in high yield.

Thus, soil samples were examined for microorganisms that could catalyze removal of the phthalamido group from a test substrate (II) that was formed by base cleavage of the phthalimido ring of a bivalently N-protected compound. A culture was identified that demonstrated phthalyl amidase activity that liberated the free amine derivative of the test substrate. Native enzyme was purified and shown to catalyze the following desired reaction:

The enzyme is stable in the broad range of pH from 6–9, having an optimum stability pH of 8.0±0.4. The enzyme also demonstrates a marked stability dependence on ionic strength. Ionic strength above 20 mM enhances pH and temperature stability of the enzyme. Optimum ionic strength occurs at 200 mM and above.

The enzyme retains good activity in low salt (50 mM) up to 30° C. and in high salt (200 mM) up to 40° C. In 200 mM salt, at least 80% of the enzyme activity is retained in temperatures up to 35° C. for 48 hours.

Iodoacetic acid (10 mM), p-HMB (1 mM), and $Cu^{++}$ (1 mM) significantly inhibited the enzyme. No organic co-factors, such as ATP, NADPH, or others, stimulated enzyme activity. EDTA, phenanthroline, and metal ions besides $Cu^{++}$ had little or no effect on enzyme activity.

The molecular weight of the enzyme is approximately 49,900, as determined by electrospray mass spectrometry, and the molecule consists of one subunit.

The $K_m$, with phthalamido carbacephem (7-

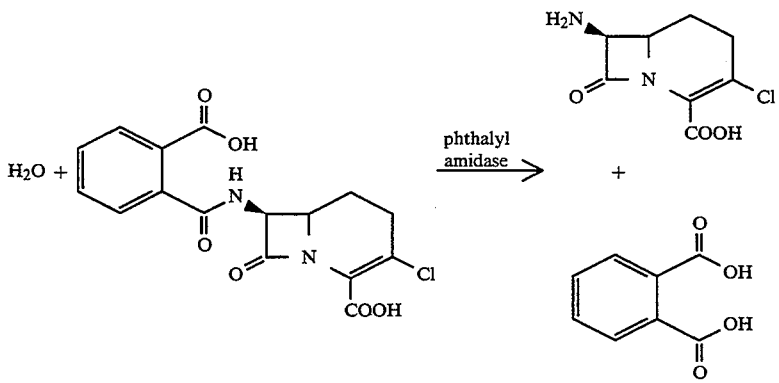

Phthalyl amidase also has significant value in peptide synthesis applications. Phthalimido amino acid derivatives are very effective reactants for enzymatic coupling of amino acids to form peptides. However, heretofore, methods for removing the phthalimido blocking group from the protected peptide were lacking. The phthalyl amidase of the current invention displays reactivity toward a wide range of substrates and can be used for deblocking phthalimido-protected peptide intermediates.

The isolated phthalyl amidase of this invention demonstrates high specific activity toward phthalylated amides or esters (i.e., having a 1,2 dicarboxylate configuration). Such compounds may have other functional groups on the phthalyl aromatic ring and still serve as substrates for the enzyme. For example, acceptable functional groups include 6-F, 6-$NH_2$, and 3-OH. Moreover, substrates may include a nitrogen in the aromatic ring ortho to the carboxyl group attached to the amine. Compounds lacking a 2-carboxylate, such as benzoyl, phenylacetate, phenoxyacetate, or their derivatives, are not suitable substrates for this enzyme.

The enzyme also exhibits a broad substrate specificity in regard to the amine group attached to the phthalate side chain. For example, phthalylated amino acids and peptides, mono- and bicyclic beta-lactams, aromatic and non-aromatic amines, as well as phthalylated amines attached to heterocycles, are dephthalylated by this enzyme at acceptable catalytic rates. The enzyme also removes the methyl group from mono-methyl phthalate.

phthalamido-3-chloro-4-carboxy-1-carba-dethioceph-3-em) (III) as substrate, is 0.9 mM in 50 mM potassium phosphate buffer, pH 8.0, and 30° C. The $V_{max}$ for this substrate and under these conditions is 7.6 µmol/min/mg.

Phthalyl amidase activity was recovered from a microorganism isolated from soil samples. The organism was characterized by comparison of its fatty acid methyl ester profile with that of known standards, and has been identified as a strain of *Xanthobacter agilis*.

The organism can be preserved as lyophilized culture and has been deposited with the National Center for Agricultural Utilization Research, 1815 North University Street, Peoria, Ill. 61604-39999, under accession number NRRL B-21115 (date of deposit: Jun. 28, 1993). Working cultures are maintained as liquid cultures stored in liquid nitrogen or at temperatures below −78° C.

In order to recover the phthalyl amidase of this invention, *Xanthobacter agilis* can be cultivated in an aqueous nutrient medium consisting of a source of carbon and nitrogen and mineral salts at an initial pH between 6 and 8 and at 25° to 37° C. A number of agents can be included in the culture medium as inducers of enzyme production, including, for example, phthalate (PAA), phthalyl glycine (PAG), and phthalyl monocyclic beta-lactam (PMBL). The enzyme can be recovered in larger amounts by cultivating *Xanthobacter agilis* in a known manner in a bioreactor of desired size, for example, with a working volume of 100 liters. Good aerating conditions, and the presence of nutrients in complex form, and a pH between 6 and 8 are important for a successful culture. The cell mass can be separated from the medium and the enzyme purified as shown in Example 4.

It will be recognized by those skilled in the art that phthalyl amidase-producing mutants of the isolated *xanthobacter agilis* organism can readily be made by methods known in the art. These mutants are considered within the scope of this invention.

As described, phthalyl amidase, catalyzes the removal of the phthalyl moiety from a wide range of phthalimido-containing compounds. The enzyme actually cleaves the amide bond of a phthalamido substrate, which is formed by the action of mild base on the corresponding phthalimido compound. This conversion proceeds readily under conditions that are suitable for enzyme activity. Thus, the phthalimido-containing compound and the enzyme being concurrently present under conditions that promote enzyme activity result in in situ removal of the phthalyl group.

In some chemical reactions involving an amine reactant, the corresponding phthalimido compound is particularly suited to high reaction yields whereas the conversion proceeds poorly with the unprotected amine or with a monovalently protected amine or even when the amine is bivalently protected by an alternative means. Thus, the current invention, which provides an economic source of phthalyl amidase, allows practical synthesis of a variety of amine products via phthalimido-protected amine intermediates.

It will be recognized that the enzyme can also be used in immobilized form to catalyze desired reactions according to procedures known in the art.

A specific application of the current invention occurs in a new chiral synthesis of the antibiotic loracarbef. The phthalyl amidase-catalyzed reaction shown above is one step of that synthesis.

Another application occurs in the synthesis of aspartame (N-L-α-aspartyl-L-phenylalanine, 1-methyl ester) as described in Example 16 below.

In both cases phthalic anhydride (or other suitable activated forms of phthalic acid) is used to react with an intermediate containing a key amino group so that a phthalimido moiety is formed for bivalent protection of the amino group. The bivalently protected amine can then be converted efficiently to a desired intermediate. For example, cyclization of a α-phthalimido-β-hydroxy-acid to a beta-lactam, or for example, condensation of an α-phthalimido carboxy-activated amino acid with a carboxy-protected amino acid to form a dipeptide. The phthalimido moiety is hydrolyzed with mild base and the resulting phthalamido moiety is then exposed to phthalyl amidase to catalyze the removal of the phthalyl moiety and release free amine plus phthalic acid.

In addition to identification and isolation of a naturally-occurring phthalyl amidase, the current invention provides DNA compounds that comprise an isolated nucleotide sequence encoding phthalyl amidase, recombinant DNA vectors encoding phthalyl amidase, host cells transformed with these DNA vectors, and a method for producing recombinant phthalyl amidase. These elements of the current invention provide the opportunity to use phthalyl amidase as a biocatalyst in industrial scale chemical processes.

Phthalyl amidase may be produced by cloning DNA encoding phthalyl amidase into a variety of vectors by means that are well known in the art. A number of suitable vectors may be used, including cosmids, plasmids, bacteriophage, and viruses. One of the principle requirements for such a vector is that it be capable of reproducing itself and transforming a host cell. Preferably, the vector will be a recombinant DNA vector that is capable of driving expression of phthalyl amidase encoded by the DNA compounds of this invention. Typical expression vectors comprise a promoter region, a 5'-untranslated region, a coding sequence, a 3'-untranslated region, an origin of replication, a selective marker, and a transcription termination site.

After the DNA compound encoding phthalyl amidase has been inserted into the vector, the vector may be used to transform a host cell. In general, the host cell may comprise any cellular organism, including a prokaryotic cell or eukaryotic cell, that is capable of being transformed with a vector comprising the DNA of this invention. The techniques of transforming and transfecting cells are well known in the art and may be found in such general references as Maniatis, et al. (1989) or *Current Protocols in Molecular Biology* (1989).

A particularly preferred method of the current invention generates soluble, extra-cellular enzyme. The method makes use of a DNA compound that comprises SEQ ID NO:6, which enables, when transformed into *Streptomyces lividans* as part of a self-replicating vector, the host to produce and secrete soluble mature phthalyl amidase in an amount in excess of the amount of a cell-bound form of the enzyme produced by *Xanthobacter agilis*, the bacterium from which the DNA compound was cloned.

SEQ ID NO:6 comprises four functional components: SEQ ID NO:7; SEQ ID NO:8; SEQ ID NO:1; and SEQ ID NO:10. SEQ ID NO:7, which includes the promoter-bearing nucleotides 1-135 of SEQ ID NO:6, promotes transcription of the coding sequences. SEQ ID NO:8 (nucleotides 136-261 of SEQ ID NO:6) encodes the signal peptide portion of a proenzyme form of phthalyl amidase (pro-phthalyl amidase (SEQ ID NO:4)). The signal peptide (SEQ ID NO:9), which provides for transport of the proenzyme across the microbial cell wall of *Streptomyces lividans*, is cleaved from the proenzyme by the cell, thereby enabling extracellular production of the mature enzyme. SEQ ID NO:1 (nucleotides 262-1620 of SEQ ID NO:6) encodes mature phthalyl amidase (SEQ ID NO:2). SEQ ID NO:10 (nucleotides 1621-3029 of SEQ ID NO:6) is a 3'-untranslated region which assists proper and efficient translation termination of the mRNA that encodes pro-phthalyl amidase.

Moreover, in a more general application of the expression method of the current invention, a wide variety of soluble, extra-cellular, properly-folded, functional proteins may be produced in Streptomyces. The current method comprises propagating *Streptomyces lividans* that has been transformed with a DNA compound, which encodes the desired enzyme, protein, or peptide, and which includes the transcriptional and translational regulatory elements of the phthalyl amidase gene isolated from the bacterium *Xanthobacter agilis*. These regulatory elements enable synthesis and secretion of the soluble, properly-folded, functional enzyme, protein, or peptide.

To accomplish the general method, the DNA sequence encoding mature phthalyl amidase (SEQ ID NO:1) may be replaced in SEQ ID NO:6 by a heterologous open reading frame from a wide variety of organisms wherein the heterologous open reading frame encodes a mature protein or hormone and introns are absent from those open reading frames, either by nature or by virtue of precise removal from genomic DNA to form cDNA open reading frames. In this arrangement, the regulatory elements of the phthalyl amidase gene continue to function such that proteins and oligopeptides other than phthalyl amidase are produced and secreted from Streptomyces transformed with the modified DNA sequence. Thus, substitution of a desired protein-encoding sequence for the coding sequence of mature phthalyl amidase enables economic extra-cellular production of numerous enzymes, peptides, and peptide hormones.

Synthesis of the phthalyl amidase gene and its various elements can be accomplished by recombinant DNA technology. Synthetic genes, the in vitro or in vivo transcription and translation of which will result in the production of the phthalyl amidase enzyme, may be constructed by techniques well known in the art. Owing to the degeneracy of the genetic code, the skilled artisan will recognize that a sizable, yet definite, number of DNA sequences may be constructed, which encode the phthalyl amidase enzyme. All such sequences are provided by the present invention.

A preferred sequence encoding phthalyl amidase is the naturally-occurring phthalyl amidase gene of *Xanthobacter agilis*, which is SEQ ID NO:6. This preferred gene is available on an 3.2 kb SacI-BamHI restriction fragment of plasmid pZPA600, which can be isolated from *Streptomyces lividans* TK23/pZPA600 by techniques well known in the art. *Streptomyces lividans* TK23/pZPA600 designates *Streptomyces lividans* strain TK23 which has been transformed with vector pZPA600.

Plasmid pZPA600 was derived by ligating SEQ ID NO:6 into Streptomyces vector, pIJ702 (Hopwood, D. A., et al., *Genetic Manipulations of Streptomyces: A Laboratory Manual*, The John Innes Foundation, Norwich, England, 1985). The pIJ702 vector contains a pIJ101 Streptomyces replicon and a thiostrepton resistance gene for selection. The ligated material was transformed into *Streptomyces lividans* TK23 by a standard protoplast fusion technique. After selection on thiostrepton (45 μg/ml), the plasmid designated pZPA600, was isolated and confirmed by restriction analysis. A restriction site and function map of plasmid pZPA600 is found in FIG. 1.

*Streptomyces lividans* TK23/pZPA600 is publicly available and on deposit at the National Center for Agricultural Utilization Research, 1815 North University Street, Peoria, Ill. 61604-39999, under accession number NRRL B21290 (date of deposit: Jun. 23, 1994). The *Streptomyces lividans* TK23 strain has been previously described in *Plasmid* 12:1936 (1984).

Plasmid pZPA600 allows high level expression of the pro-phthalyl amidase open reading frame and results in secretion of soluble mature phthalyl amidase, which process is especially preferred. Thus, the invention comprises a process in which *Streptomyces lividans* TK23/pZPA600 is grown and then separated from its extra-cellular broth so that high concentrations of phthalyl amidase are obtained in that cell-free broth.

Other preferred sequences include, for example, SEQ ID NO:1, which encodes mature phthalyl amidase enzyme (SEQ ID NO:2), and SEQ ID NO:3, which encodes the proenzyme form of phthalyl amidase (SEQ ID NO:4). Thus, the present invention also comprises plasmid pZPA400 as a preferred embodiment.

Figure 2:
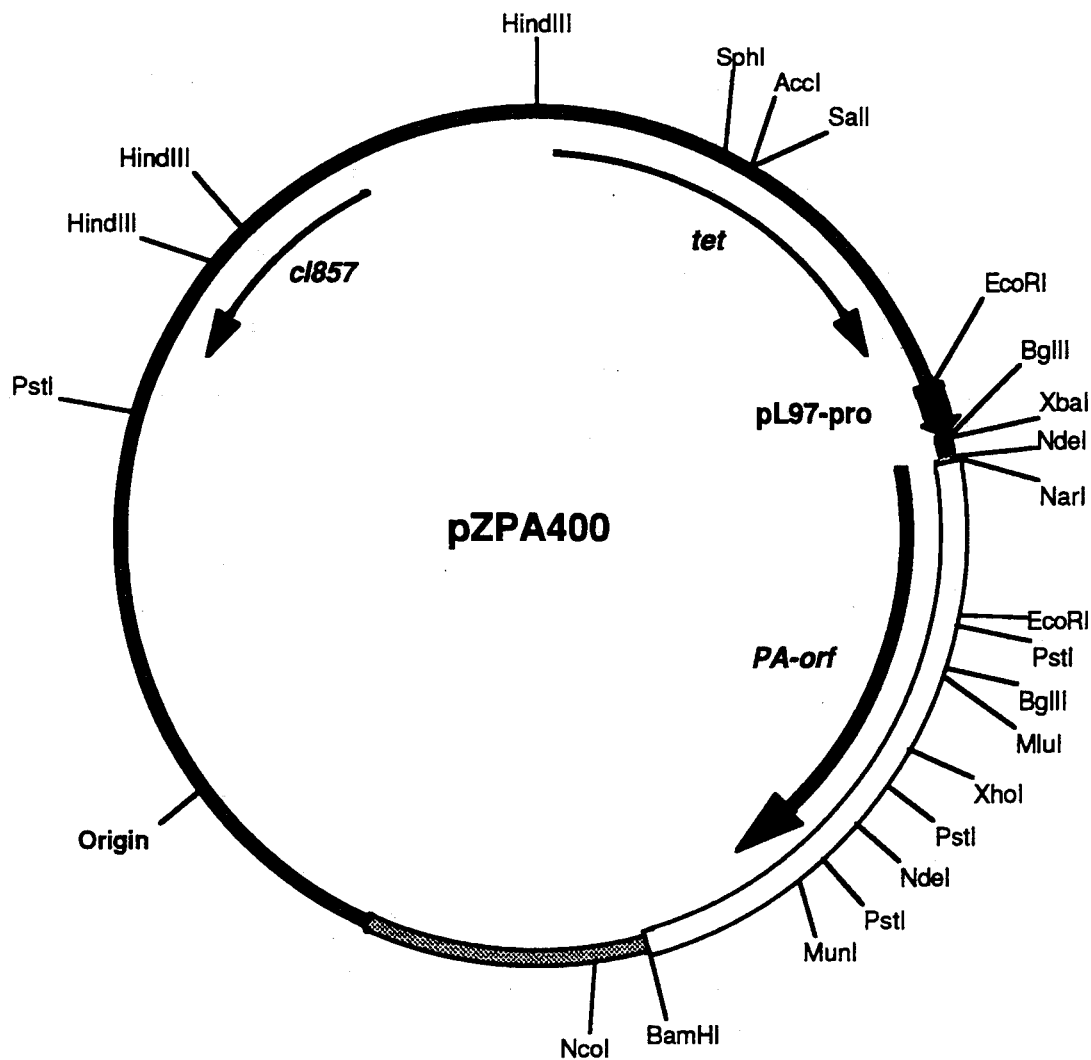
FIG. 2 is a restriction enzyme site and function map of plasmid pZPA400.

In plasmid pZPA400, the 5'-regulatory elements of the native gene were removed and an ATG codon for a methionyl residue was attached to the 5'-terminal nucleotide of the mature phthalyl amidase coding sequence to generate an open reading frame (SEQ ID NO:11) encoding met-phthalyl amidase (SEQ ID NO:12). SEQ ID NO:11 was positioned, via a two-cistron configuration, such that transcription was driven by a temperature inducible lambda pL promoter. Plasmid pZPA400 also contains the temperature sensitive cI857 repressor gene, a tetracycline resistance gene, and the pBR322-based origin of replication minus the rop region, which controls copy number (Cesareni et al., *Proc. Natl. Acad. Sci.* 79:6313, 1982). *E. coli* cells harboring this plasmid (*E. coli* DH5α/pZPA400) are induced to produce met-phthalyl amidase (without signal peptide) when the culture temperature is raised from 30° C. to 42° C. A restriction site and function map of plasmid pZPA400, which can be isolated from *E. coli* DH5α/pZPA400 cells by techniques well known in the art, is found in FIG. 2.

*E. coli* DH5α/pZPA400 designates the commercially available *E. coli* DH5α strain that has been transformed with plasmid pZPA400. *E. coli* DH5α/pZPA400 cells are publicly available and on deposit at the National Center for Agricultural Utilization Research, 1815 North University Street, Peoria, Ill. 61604-39999, under accession number NRRL 21289 (date of deposit: Jun. 23, 1994).

The phthalyl amidase gene may also be created by synthetic methodology. Such methodology of synthetic gene construction is well known in the art. See Brown et al. (1979) *Methods in Enzymology*, Academic Press, New York, 68:109. The phthalyl amidase DNA sequence may be generated using a conventional DNA synthesizing apparatus, such as the Applied Biosystems Model 380A of 380B DNA synthesizers (commercially available from Applied Biosystems, Inc., 850 Lincoln Center Drive, Foster City, Calif. 94404.

Synthesis of the phthalyl amidase protein of the present invention may also proceed by solid phase synthesis. The principles of solid phase chemical synthesis of polypeptides are well known in the art and may be found in general texts, such as, Dugas, H. and Penny, C., *Bioorganic Chemistry* (1981), Springer-Verlag, New York, pp. 54–92. However, recombinant methods are preferred if a high yield is desired.

A skilled artisan will recognize that the nucleotide sequences described in the present disclosure may be altered by methods known in the art to produce additional sequences that substantially correspond to the described sequences without changing their functional aspects. These altered sequences are considered to be included in the current invention.

In order that the invention described herein may be more fully understood, the following examples are set forth. It should be understood that the examples are for illustrative purposes only and are not to be construed as limiting the scope of the invention.

EXAMPLE 1

Search for phthalyl amidase producing organisms 240 soil samples (8 to 15 mg of damp dry soil) were individually suspended in 10 ml sterile BL medium (hereinafter defined) containing 100 mg phthalyl monocyclic beta-lactam (PMBL) (I).

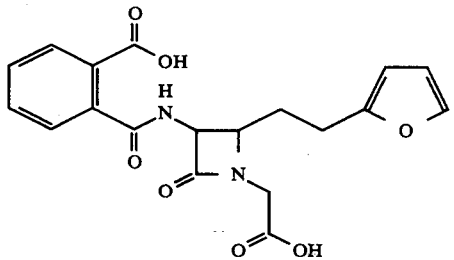

BL medium had the following composition:

| | |
|---|---|
| Na₂HPO₄ | 6.0 g |
| KH₂PO₄ | 3.0 g |
| NaCl | 0.5 g |
| NH₄Cl | 2.0 g |
| CaCl₂ | 0.1 g |
| MgSO₄.7H₂O | 0.25 g |
| ZnSO₄.7H₂O | 70 mg |
| FeCl₃.6H₂O | 270 mg |
| MnSO₄ | 80 mg |
| CuCl₂ | 7.4 mg |
| CoSO₄.7H₂O | 28 mg |
| H₃BO₃ | 3 mg |
| Yeast Extract | 1.0 g |
| Deionized water | 1.0 L |
| pH | 7.0 |

The cultures were incubated aerobically at 30° C. in a rotary shaker at 250 rpm for as long as 2 weeks. Cultures were examined by thin layer chromatography at 7 day intervals for the disappearance of the starting substrate and appearance of the beta-lactam nucleus product.

A culture showing the desired catalytic activity was transferred at least two more times under similar conditions of medium and growth. The final culture was diluted with sterile water and plated out on agar plates containing either Trypticase Soy Broth (Difco) or Bac MI medium. Bac MI medium had the following composition:

| | |
|---|---|
| Peptone | 10.0 g |
| Beef Extract | 5.0 g |
| Yeast Extract | 2.0 g |
| NaCl | 5.0 g |
| Deionized water | 1.0 L |
| pH | 7.0 |

(Agar plates were prepared by adding 20 g agar per L of medium).

Individual colonies were picked from the agar and grown in Bac MI medium containing 10 mg/ml of PMBL for 12 days at 30° C. with aeration. Broths were examined for appearance of beta-lactam nucleus and phthalic acid using TLC.

A pure isolated organism that demonstrated rapid hydrolysis of the substrate was then grown in Bac MI medium containing 1 mg/ml phthalate for 48 hours at 30° C. with aeration. Cells were centrifuged and then suspended in 50 mM Tris-HCl buffer, pH 8.0, at a ratio of 1 g wet weight cells to 8 ml of buffer. A solution of lysozyme, 2 mg in 1.0 ml 50 mM EDTA, pH 8.2, was added at the ratio of 1 ml lysozyme solution to 8 ml cell suspension. After mixing well and holding at room temperature for 1 hour, the suspension was cooled to 4° C. and held overnight. The resultant viscous solution was sonicated only long enough to liquefy the solution. This solution was centrifuged at 10,000 rpm for 15 minutes. The pellet was discarded and the supernatant tested for phthalyl amidase activity.

The cell-free extract was chromatographed on a size exclusion column (1.5×100 cm; Sephacryl S-300; Pharmacia, Piscataway, N.J.) at 4° C. with an elution buffer consisting of 50 mM potassium phosphate and 150 mM KCl at a flow rate of 0.5 ml/min. The eluant was monitored at a wavelength of 280 nm. UV-absorbing fractions were tested for hydrolysis of PMBL by HPLC.

Reference proteins for molecular weight (daltons) determination were chymotrypsinogen (25,000), ovalbumin (43,000), albumin (67,000), aldolase (158,000), catalase (232,000), ferritin (440,000), and thyroglobulin (669,000).

Cell-free extract of the organism subsequently identified as *Xanthobacter agilis* was determined to contain an enzyme that catalyzed the hydrolysis of PMBL, and which had an approximate molecular weight of 54,000 daltons and a specific activity of 39.7 nmol/min/mg.

EXAMPLE 2

Production of phthalyl amidase from *Xanthobacter agilis*

Fermentation of *Xanthobacter agilis* on a 100 L scale was conducted in 100 L working volume bioreactors, with automatic control for pH (7.9–8.1), temperature (30° C.), air flow (1 scfm), agitation (300 rpm), and back pressure (5 lb). Dissolved oxygen levels (>50%) were kept constant by small increases in agitation speed. The medium consisted of 1.25% Bacto peptone, 0.3% yeast extract, 0.5% beef extract, 0.5% phthalic acid, 0.5% NaCl, and 0.05% anti-foam. After sterilization, the medium was brought to pH 8.0 with 30% sulfuric acid. The fermenter was inoculated with 1 L of pre-culture which had been incubated at 30° C. for 24 hours in the same medium with shaking at 300 rpm. After 48 hours of growth, the fermentation broth was cooled and centrifuged at 17,000 rpm with a flow rate of 1 to 2 L/min to remove the biomass. The cell paste was harvested and stored at −20° C. yielding 6.0 g wet cell weight/L.

EXAMPLE 3

Induction of phthalyl amidase

Three compounds at different concentrations were added to aerated cultures of the organism growing at 30° C. in Bac MI medium. The compounds tested were phthalate (PAA), phthalyl glycine (PAG), and PMBL. Cells of *Xanthobacter agilis* were grown with aeration for 24 hours. This vegetative culture was used to inoculate Bac MI medium (50 ml) containing different concentrations of the compounds to be tested. After 48 hours growth under standard conditions, cells were harvested by centrifugation and wet weight of the cells was determined. Crude cell extracts were prepared by lysozyme treatment of the cells as in Example 1. Suspensions were briefly sonicated to break up the viscous suspension. A cell-free supernatant was obtained by centrifugation of the suspension at 14,000 rpm for 15 minutes.

Enzyme activity in cell-free lysates was determined by monitoring conversion of the chromogenic substrate 4-(2′-carboxy-N-benzoyl)amino-2-carboxy-nitrobenzene (II) to 2-nitro-5-amino benzoic acid and phthalic acid, a reaction catalyzed by phthalyl amidase as shown below:

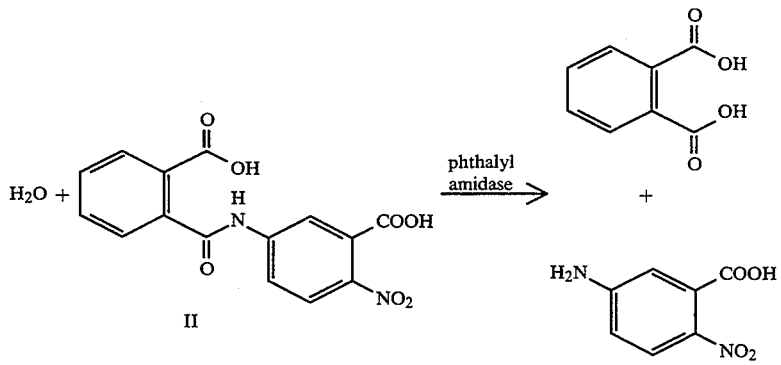

The assay reaction mixture (1 ml) consisted of 0.3 μmol of the chromogenic substrate (II) and 0.001–0.5 μg of enzyme preparation in 50 mM potassium phosphate buffer, pH 8.0 (buffer A). The enzymatic reaction was conducted at 30° C. for 10 minutes and the appearance of product was monitored at 380 nm (or 430 nm). The amount of substrate hydrolyzed was calculated from a standard curve of the amine product.

As can be seen in Table 1, PAG and PAA increased the wet weight cell mass while PMBL had no effect. However, all three substrates produced a dramatic concentration-dependent increase in the total number of enzyme units recovered. The units of enzyme per gram of wet weight cells also increased with all additions but the increase was most pronounced at high PAA concentrations.

TABLE 1

| Inducer | Addition (mg/ml) | Cell weight (g/50 ml) | Total units/ mg protein (μmol/min/mg) | Units/ g cells |
|---|---|---|---|---|
| Control | — | 0.29 | 0.017 | 0.06 |
| PAG | 1 | 0.33 | 0.35 | 1.04 |
|  | 5 | 0.5 | 4.4 | 9.4 |
| PMBL | 1 | 0.35 | 0.28 | 0.79 |
|  | 5 | 0.24 | 2.0 | 8.1 |
| PAA | 1 | 0.35 | 1.4 | 3.9 |
|  | 2 | 0.47 | 4.3 | 9.3 |
|  | 5 | 0.7 | 3.7 | 5.5 |
|  | 10 | 0.6 | 12.0 | 19.8 |

EXAMPLE 4

Purification of phthalyl amidase

A. Analytical scale purification of phthalyl amidase

Cells of *Xanthobacter agilis* (200 grams, wet weight), which contained significant amounts of phthalyl amidase activity, were resuspended to 1800 ml in 50 mM Tris-HCl, pH 8.0, plus 5 mM EDTA. The cells were broken by sonication for 22 minutes at a maximal power below 8° C. DNase (1 μg/ml) and magnesium sulfate (10 mM) were added during the sonication to minimize viscosity and improve cell breakage. After a high-speed centrifugation, the resulting crude extract supernatant served as the source for further enzyme purification. All subsequent purification steps were conducted at 4° C.

The crude extract was loaded onto a Q-Sepharose column (4.4×23 cm; Pharmacia), previously equilibrated with buffer A. After washing with buffer A, a linear gradient of 0–1.5M KCl in buffer A was applied and the phthalyl amidase eluted as a single activity peak between 1 and 1.1M KCl. Selected fractions containing most of the enzyme activity were pooled as Q-Sepharose eluate.

The Q-Sepharose eluate was subjected to ammonium sulfate fractionation. The majority of the enzyme activity was recovered from 67–77, 77–87 and 87–97% ammonium sulfate pellets. Those pellets were solubilized in buffer A with 0.2M ammonium sulfate.

Ammonium sulfate was added to the 67–97% ammonium sulfate enzyme pool to a final concentration of approximately 2M. The enzyme pool was loaded onto a Phenyl-Sepharose column (2.6×16 cm; Pharmacia), which was previously equilibrated with buffer A plus 2.6M ammonium sulfate. The phthalyl amidase eluted with a linear gradient decreasing from 2.6M to 0M ammonium sulfate in buffer A as a single activity peak between 0M and 0.5M ammonium sulfate. Selected fractions containing the majority of the enzyme activity were pooled as Phenyl-Sepharose eluate.

The Phenyl-Sepharose eluate was dialyzed against buffer A and then loaded onto a hydroxylapatite column (1.5×90 cm; Clarkson Chemical Company, Williamsport, Pa.), which was previously equilibrated with buffer A. After washing the column with buffer A, the enzyme eluted with a linear gradient of 50–500 mM potassium phosphate, pH 8.0, as a single activity peak between 150 and 190 mM potassium phosphate. Selected fractions containing most of the enzyme activity were pooled as hydroxylapatite eluate.

After a dilution of the buffer strength from 120 to 50 mM potassium phosphate, the hydroxylapatite eluate was loaded onto a Mono P column (0.5×20 cm; Pharmacia), which was previously equilibrated with buffer A. After washing with 3 column volumes of buffer A, a linear gradient of 0–1.5M KCl in buffer A was applied and the enzyme eluted as a single activity peak between 0.72 and 0.8M KCl. Those fractions containing the majority of the enzyme activity were pooled as Mono P eluate. The most active enzyme preparation was derived from Mono P FPLC (Fast Protein Liquid Chromatography).

Table 2 summarizes the results of the purification. Based on sodium dodecyl sulfate-polyacrylamide gel electrophoresis (SDS-PAGE) and Laser Densitometric Scanning, the phthalyl amidase was greater than 95% pure.

The phthalyl amidase activity reported in Table 2 was determined using the chromogenic substrate as in Example 3. A typical reaction mixture in a total volume of 1 ml contained 0.2 mg of the chromogenic substrate and an aliquot of phthalyl amidase in buffer A. The enzymatic reaction was conducted at 30° C. for 10–15 min. Formation of the reaction product was monitored with a spectrophotometer at 430 nm (or 380 nm) and quantitated from a standard curve of the product.

TABLE 2

| Step | Protein (mg) | Activity (Units) | Spec. Act. (Units/mg) | Purification (fold) | Yield (%) |
| --- | --- | --- | --- | --- | --- |
| Crude Extract | 5475 | 345 | 0.063 | 1 | 100 |
| Q Sepharose | 230 | 279 | 1.214 | 19 | 81 |
| Ammonium Sulfate: 67-97% cut | 145 | 224 | 1.547 | 25 | 65 |
| Phenyl-Sepharose | 63 | 158 | 2.505 | 40 | 46 |
| Hydroxyl-apatite | 28 | 154 | 5.52 | 88 | 45 |
| Mono P | 16.5 | 119 | 7.2 | 119 | 34 |

B. Preparative scale purification of phthalyl amidase

Crude extract of *Xanthobacter agilis* was prepared by adding 1 g of cells (wet weight) and 2 mg lysozyme per 9 ml of 50 mM Tris-HCl buffer, pH 8.0, 1 mM EDTA (600 g cells total). After 30 minutes at room temperature, DNase (100 U/g of cells) in 10 mM magnesium sulfate was added. The cells were homogenized using a cell homogenizer for 30 minutes at room temperature. After 17 hours of incubation at 8° C., the lysate was centrifuged at 10,000 rpm for 30 minutes.

The crude extract supernatant (4.5 L) was applied to a Super-Q column (7×40 cm; TosoHaas, Montgomeryville, Pa.) equilibrated in buffer A. After loading crude extract, the column was washed with 2 column volumes of 50 mM phosphate buffer containing 3.5M urea, pH 8.0. A second wash (5 L) was used to re-equilibrate the column in buffer A. Phthalyl amidase eluted from the column using a 10 column-volume linear gradient of 0-1.5M KCl in buffer A. Fractions were collected and assayed for enzyme activity. The active fractions were pooled (1.5 L), concentrated (250 ml), and diafiltered with buffer A at 7°-10° C.

The concentrated and diafiltered Super-Q mainstream was applied to a hydroxylapatite column (3.2×40 cm) equilibrated in buffer A. After washing the column with this buffer, phthalyl amidase was eluted using a linear gradient of 0-500 mM phosphate buffer, pH 8.0. Fractions were assayed according to the chromogenic substrate method (see Example 3) and the active fractions were pooled (1 L) and concentrated (400 ml).

Table 3 shows the results of this purification.

TABLE 3

| Step | Activity (Units) | Spec. Act. (Units/mg) | Purification (Fold) | Yield (%) |
| --- | --- | --- | --- | --- |
| Crude Extract | 14,846 | 0.8 | 1 | 100 |
| Super-Q | 6,828 | 3.0 | 4 | 46 |
| Hydroxyl-apatite | 4,985 | 9.0 | 11 | 34 |

EXAMPLE 5

Effect of pH on phthalyl amidase activity

The effect of pH on the reaction rate of the analytical scale purified enzyme was determined using phthalamido carbacephem (III) as substrate.

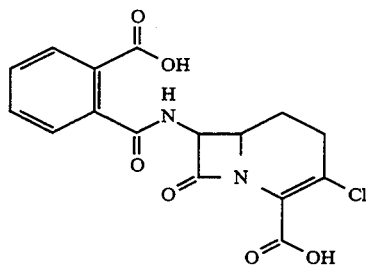

III

A typical reaction mixture consisted of 1 ml total volume and contained 0.1 mM III, 0.1 μM phthalyl amidase in 50 mM potassium phosphate buffer (pH 5.5-9.0) at 32° C. for 20 minutes. The reactions were stopped by the addition of 1 ml methanol. After removal of precipitate by centrifugation, an aliquot of the supernatant fraction (typically 30 μ) was monitored for the beta-lactam nucleus and phthalic acid by HPLC using a Zorbax C8 column (0.46×15 cm; MacMod Analytical Inc., Chadds Ford, Pa.). The two reaction products were eluted by a mobile phase constructed as continuous mixed gradients from (a) 1% ACN (acetonitrile)/0.2% TFA (trifluoroacetic acid) and (b) 80% ACN/0.2% TFA as follows: 1) 0% (b), 3 min; 2) 0-50% (b), 0.5 min; 3) 50-100% (b), 3 min; 4) 100% (b), 2.5 min; 5) 100-0% (b), 0.1 min; and 6) 0% (b), 5 min. At a flow rate of 1.5 ml/min, retention times of the beta-lactam nucleus and phthalic acid, as measured at 254 nm, were 2.3 and 7.2 min, respectively.

The results are shown in Table 4. Optimal range for enzyme activity occurred between pH 7.8 and 8.4.

TABLE 4

| pH | Specific Activity (μmol/min/μmol enzyme) |
| --- | --- |
| 7.0 | 125.4 |
| 7.2 | 130.4 |
| 7.4 | 155.2 |
| 7.6 | 172.5 |
| 7.8 | 184.2 |
| 8.0 | 195.3 |
| 8.2 | 201.2 |
| 8.4 | 208.0 |
| 8.6 | 181.7 |
| 8.8 | 185.1 |
| 9.0 | 33.1 |

EXAMPLE 6

Optimum reaction temperature

Test reactions were carried out similar to Example 5 except that all incubations were performed in 50 mM potassium phosphate buffer at pH 8.2. Solutions of the substrate were pre-incubated for 5 minutes at temperatures between 2° and 60° C. The enzymatic reaction was initiated by the addition of phthalyl amidase and stopped by the addition of 1 ml methanol. Specific activity of the enzyme was determined by monitoring the hydrolysis of III by HPLC as in Example 5.

The maximum reaction rate for the enzyme was reached at 34° C. Little enzyme activity was found below 10° C. and above 50° C.

EXAMPLE 7

Optimum salt concentration

Test reactions were carried out similar to Example 6 except that buffer concentrations ranging from 10 to 200 mM at 32° C. were examined. All other conditions and analyses were the same.

As is apparent in Table 5, high salt concentration markedly improved the specific activity of the enzyme. The effect was of a general nature and did not appear to be dependent on specific anions or cations.

TABLE 5

| Buffer Conc. | Specific Activity (μmol/min/μmol enzyme) | | |
| --- | --- | --- | --- |
| (mM) | K Phosphate | Tris-HCl | NH4 Acetate |
| 10 | 148 | 73 | 25 |
| 50 | 300 | 230 | 50 |
| 100 | 350 | 275 | 75 |
| 200 | 360 | 300 | 100 |

EXAMPLE 8

Stability of phthalyl amidase
A. Effect of ionic strength

The stability of phthalyl amidase at pH values ranging from 6–9 was determined as described in Example 5 at 30° C. in both 20 and 200 mM potassium phosphate buffer. In 20 mM buffer, all enzyme activity was lost within 2 hours at any pH of the incubation medium. In 200 mM buffer, the enzyme retained at least 80% of its activity for 100 hours irrespective of the pH of the incubating medium. Twenty mM buffer that was supplemented with 200 mM KCl or NaCl also protected against activity loss, indicating that the enzyme stabilization was primarily dependent on the high ionic strength of the buffer.

B. Temperature stability

The phthalyl amidase enzyme was also tested for stability at varying temperatures. The enzyme was incubated at pH 8.2 in the temperature range of 4°–50° C. for 48 hours in 50 and 200 mM phosphate buffer. In 50 mM buffer, the enzyme retained 90% of its activity for 48 hours when maintained at temperatures below 25° C., while all enzyme activity was lost within 48 hours when the incubation temperature was above 40° C. In 200 mM buffer, 80% of the enzyme activity was retained in temperatures up to 35° C. and 30% of the enzyme activity was retained after 48 hours incubation at 40° C.

EXAMPLE 9

Influence of effectors on enzyme activity

The effect of various agents on the enzymatic activity of phthalyl amidase was determined using standard conditions (see Example 5). All agents were tested at 1 mM final concentration unless otherwise indicated.

It can be seen from the data in Table 6 that iodoacetate, p-HMB, and copper ions significantly reduced phthalyl amidase activity. None of the tested compounds stimulated enzyme activity significantly above that of the control.

Table 7 shows the effects of four organic solvents at three concentrations on enzyme catalysis. All four solvents tested significantly decreased enzyme activity at a concentration of 10%. Glycerol caused the least amount of inhibition of the enzyme at the highest concentration tested.

TABLE 6

| Effector Agent | % of Control Activity |
| --- | --- |
| Sulfhydryl agents | |
| p-HMB | 65 |
| DTNB | 98 |
| NEM | 100 |
| Iodoacetate, 1 mM | 91 |

TABLE 6-continued

| Effector Agent | % of Control Activity |
| --- | --- |
| Iodoacetate, 10 mM | 46 |
| Metal chelators | |
| Phenanthroline | 104 |
| EDTA | 103 |
| Cofactors and reducing agents | |
| Mercaptoethanol | 105 |
| DTT | 100 |
| NAD | 101 |
| NADH | 96 |
| NADP | 99 |
| NADPH | 99 |
| ATP | 96 |
| PLP | 106 |
| THF | 100 |
| CoASH | 102 |
| THF + DTT | 100 |
| FAD | 101 |
| FAD + DTT | 100 |
| Metal Cations | |
| NaCl | 104 |
| KCl | 100 |
| CaCl2 | 89 |
| CoCl2 | 101 |
| CuCl2 | 36 |
| FeCl2 | 102 |
| FeCl3 | 96 |
| MgCl2 | 102 |
| MnCl2 | 84 |
| NiCl2 | 94 |
| ZnCl2 | 100 |

DTT: dithiothreitol
p-HMB: para-hydroxy mercuric benzoate
DTNB: dithionitrobenzoate
NEM: N-ethylmaleimide
NAD: nicotinamide adenine nucleotide
NADP: nicotinamide adenine dinucleotide phosphate
NADPH: reduced form of NADP
ATP: adenosine 5'-triphosphate
PLP: pyridoxyl-5-phosphate
THF: tetrahydrofolate
FAD: flavin adenine dinucleotide

TABLE 7

| | % Residual enzyme activity | | |
| --- | --- | --- | --- |
| Solvent | 1.0% | 5.0% | 10.0% |
| Ethanol | 99 | 85 | 45 |
| DMSO | 101 | 80 | 71 |
| Glycerol | 100 | 94 | 85 |
| Methanol | 100 | 90 | 69 |

DMSO: dimethyl sulfoxide

EXAMPLE 10

Physical and chemical properties of phthalyl amidase

The molecular weight of the phthalyl amidase was determined to be 49,900 by electrospray mass spectrometry. The enzyme is monomeric with an isoelectric point estimated by isoelectric focusing to be pH 5.5. Chemical hydrolysis and amino acid analysis of the protein by standard methods are shown in Table 8. Repeated attempts to sequence the N-terminus of the purified enzyme failed, indicating that the enzyme was blocked.

TABLE 8

| Amino Acid | Number of residues in protein |
| --- | --- |
| Aspartate/Asparagine | 62 |
| Threonine | 21 |
| Serine | 37 |
| Glutamate/Glutamine | 52 |
| Proline | 26 |
| Glycine | 34 |

TABLE 8-continued

| Amino Acid | Number of residues in protein |
|---|---|
| Alanine | 50 |
| Cysteine* | 2 |
| Valine | 23 |
| Methionine | 12 |
| Isoleucine | 20 |
| Leucine | 35 |
| Tyrosine | 17 |
| Phenylalanine | 13 |
| Histidine | 11 |
| Lysine | 4 |
| Arginine | 20 |
| Tryptophan* | 13 |

*derived from nucleotide sequence of the gene

EXAMPLE 11

Substrate specificity of phthalyl amidase

A. Chemical structure requirements for enzyme activity

The activity of phthalyl amidase against 25 compounds was determined. The compounds were divided into beta-lactams (Table 9), phthalyl amides (Table 10), and aromatic ring substituted amides (Table 11). Each reaction mixture (1 ml total volume) contained 2.5 μmol of compound and 0.3 units of enzyme (based on the chromogenic substrate) of the preparative scale purified enzyme, in 50 mM phosphate buffer, pH 8.0. The reactions were conducted at 30° C. Samples of the reaction mixture were taken at various times, and methanol (equal volume) was added to stop the reaction. The samples were examined by HPLC to determine the extent of substrate hydrolysis. The amount of compound hydrolyzed was calculated from a standard curve of the test compound. All substrates were stable in buffer at 30° C. and pH 8.0 in the absence of enzyme for 24 hours.

As the results in Table 9 indicate, the enzyme recognizes mono- and bicyclic beta-lactam compounds containing a phthalyl group attached to the exocyclic nitrogen. However, the side chain apparently requires a 2-carboxylate group, for example, phthalate, since no hydrolysis is observed in the absence of this functional group.

A wide variety of phthalyl amides are substrates for the enzyme as shown in Table 10. Substrates include phthalylated amino acids, dipeptides, monocyclic and bicyclic beta-lactams, phenyl, benzyl, and aliphatic amines. The enzyme also exhibited esterase activity as demonstrated by its ability to hydrolyze phthalate mono methyl ester (IX). In this series, compound XIII was the most active compound found.

Using compound XIII as a standard, a variety of aromatic ring substituted compounds were examined for reactivity with the enzyme. Results are shown in Table 11. Aromatic ring substituents at the 6 position of the phthalyl ring such as F and $NH_2$ were accepted by the enzyme. A hydroxyl group at the 3 position (XXI) of the ring and a nitrogen within the aromatic ring (XX) is also acceptable. Low levels of hydrolysis occur if a tetrazole is substituted for the 2-carboxylate group (XXII). Moving the carboxylate group to the 3 (XXIV) or 4 (XXIII) position of the aromatic ring completely eliminates hydrolytic activity. Compounds lacking the 2-carboxylate (XXV-XXVIII) are not suitable substrates for the enzyme.

These results are consistent with the enzyme being a novel catalyst that removes phthalyl protecting groups from a variety of amines under mild conditions.

TABLE 9

| Compound number | Structure | Relative activity |
|---|---|---|
| I | 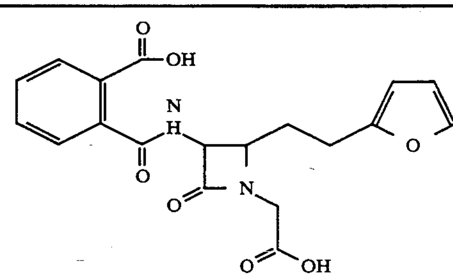 | 47.9 |
| III | 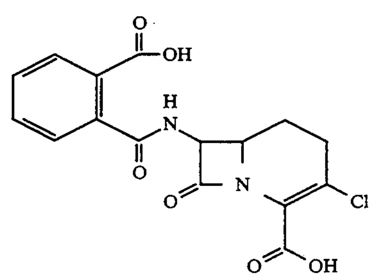 | 100 |

TABLE 9-continued
| Compound number | Structure | Relative activity |
|---|---|---|
| IV | 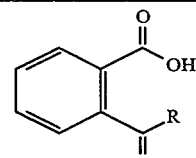 | 0 |
| V | 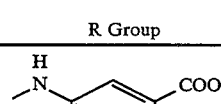 | 0 |
| VI | 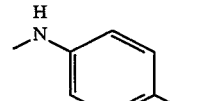 | 0 |
TABLE 10
| Compound number | R Group | Relative Activity |
|---|---|---|
| II | 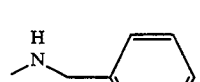 | 295.7 |
| III | 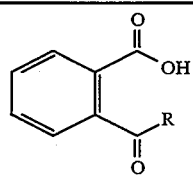 | 100.0 |
TABLE 10-continued
| Compound number | R Group | Relative Activity |
|---|---|---|
| VIII | ![p-nitro-N-methylaniline] | 544.6 |
| IX | —OCH$_3$ | 207.6 |
| X | ![N-methylbenzylamine] | 40.2 |
| XI | ![N-methylglycine] | 31.8 |

TABLE 10-continued

[Structure: phthalic acid derivative with R group]

| Compound number | R Group | Relative Activity |
|---|---|---|
| XII | H, -N-< (dimethylamino) | 9.7 |
| XIII | H, -N- (imidazolyl with hexyl-CH-COOH chain) | 1027.2 |
| XIV | —L—Asp—L—Phe—OMe | 118.5 |
| XV | -D,L-methionine | 220.1 |
| XVI | -D,L-leucine | 90.2 |

TABLE 11

[Structure: substituted benzamide with imidazole and hexyl-CH-COOH]

| Compound number | R Group | Relative Activity |
|---|---|---|
| XVII | 2-COOH | 100.0 |
| XVIII | 6-F, 2-COOH | 159.00 |
| XVIX | 6-NH₂, 2-COOH | 10.2 |
| XX | 2-COOH (with N at position 6) | 85.9 |
| XXI | 3-OH, 2-COOH | 1.3 |
| XXII | [triazole structure] at position 2 | 0.2 |
| XXIII | 4-COOH | 0 |
| XXIV | 3-COOH | 0 |
| XXV | 2-OH | 0 |
| XXVI | 3-OH | 0 |
| XXVII | 3,5-OH | 0 |
| XXVIII | 2-H | 0 |

B. Kinetic parameters for phthalyl amidase

The kinetic parameters of the enzyme were determined for several representative substrates. Compounds II, XVII, and XVIII were tested using 0.9 μg/ml of enzyme. Compounds III and XI were tested using 5.14 μg/ml of enzyme. Substrate concentrations were between 0 and 25 mM and reaction time was between 2 and 20 minutes, depending on the substrate used. All reactions were run at 32° C. and at pH 8.2. The $K_m$, $V_{max}$, $K_{cat}$, and $K_{cat}/K_m$ for these substrates are shown in Table 12. $K_m$ is the Michaelis constant for enzyme kinetics, $V_{max}$ is the maximal rate of reaction calculated by the Michaelis-Menten equation, and $K_{cat}$ is the catalytic constant for an enzyme reaction.

TABLE 12

| Parameter | II | III[a] | XI | XVII | XVIII[b] |
|---|---|---|---|---|---|
| $K_m$ (mM) | 0.05 | 0.9 | 0.14 | 0.09 | 0.17 |
| $V_{max}$ (μmol/min/mg) | 5.95 | 7.6 | 0.27 | 1.41 | 1.94 |
| $K_{cat}$ (μmol/sec/μmol) | 4.95 | 6.33 | 0.22 | 1.18 | 1.61 |
| $K_{cat}/K_m$ | 99.0 | 7.0 | 1.6 | 13.1 | 9.5 |

[a]carbacepham nucleus (7-amino-3-chloro-4-carboxy-1-carba-dethioceph-3-em ) (XXXIV) quantitatively monitored as the product of substrate III.
[b]for the other substrates, phthalic acid was the product monitored during the reaction.

C. Chiral and additional substrate selectivity of phthalyl amidase.

Several additional substrates were tested in a total volume of 1 ml. Reaction mixtures contained 0.009 mg (0.6 units) of enzyme, 2.5 μmol of substrate, and buffer A. All reactions were run at 30° C. for 2 minutes except for compounds XXX and XXXII, which were run for a longer time period since they were poor substrates for the enzyme. Reactions were stopped by the addition of methanol, and phthalic acid formation was monitored by HPLC. Results are shown in Table 13.

The results show that the enzyme has a marked preference for the D isomer of N-phthalyl-phenylglycine. The L isomer was an extremely poor substrate for the enzyme. Compound XXXI had a relative activity twice that of compound III as a substrate for the enzyme. However, by substituting a sulfonate group for the carboxyl group of the phthalyl moiety, enzyme reactivity is completely lost. Again, these results show the selectivity of this enzyme for N-phthalylated amines and indicate that the enzyme has a chiral preference on the amine side of the substrate.

TABLE 13

| Compound Number | Structure | Relative Activity |
|---|---|---|
| III | 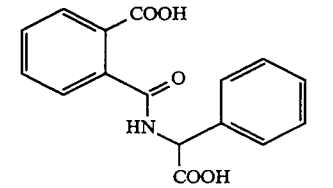 | 100 |
| XVIX | 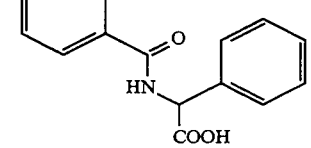<br>D-isomer | 136 |

TABLE 13-continued

| Compound Number | Structure | Relative Activity |
|---|---|---|
| XXX | (L-isomer, benzoic acid with amide to CH(COOH)Ph) | 1.3 |
| XXXI | (2-carboxy-N-phenylbenzamide) | 200 |
| XXXII | (2-SO₃K-N-phenylbenzamide) | 0.0 |

EXAMPLE 12

Preparative scale synthesis of carbacephem nucleus

Phthalimido carbacephem (XXXIII) readily hydrolyzes to phthalamido carbacephem (III) in buffer at pH 8.0. Thus, either compound XXXIII or III can be used to prepare the carbacephem nucleus (XXXIV). Substrate (4 grams) was added to 20 ml of deionized water and the pH of the solution was adjusted to 8.0 with concentrated ammonium hydroxide. Phthalyl amidase, 80 units as determined using the chromogenic substrate (II), was added to start the reaction. Temperature was maintained at 30° C. and the pH maintained at 8.0 by adding 2N ammonium hydroxide. After 510 minutes under these conditions, HPLC analysis of the samples from the reaction indicated that compound III was 90.0% hydrolyzed and compound XXXIII was 98% hydrolyzed. The pH of the reaction was lowered to 5.0 thereby precipitating the carbacephem nucleus. Isolated yields of the nucleus were between 65% and 77%.

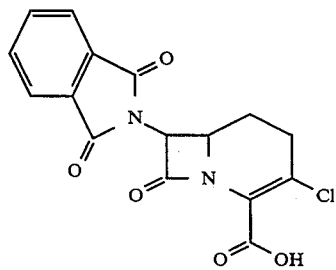

XXXIII

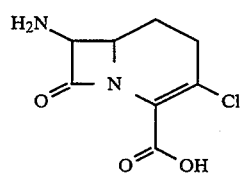

XXXIV

EXAMPLE 13

Expression of met-phthalyl amidase in *Escherichia coli*

Several small scale temperature inductions of *E. coli* DH5α/pZPA400 were carried out to assess the amount of met-phthalyl amidase protein and enzymatic activity generated by *E. coli* DH5α/pZPA400. Enzymatic activity was observed by incubation of a soluble cell extract with the chromogenic substrate (II) under conditions as described in Example 3 or with substrate III as described in Example 5. Results are reported in Table 14.

SDS-PAGE gels of the cell extract showed a Coomassie-stained protein band corresponding to approximately 50,000 daltons that increased upon temperature induction. Partial purification of the cell extract by anion exchange chromatography yielded fractions with increased phthalyl amidase specific activity. Phthalyl amidase in these fractions catalyzed cleavage of the phthalyl group from compound III to form compound XXXIV and phthalic acid.

EXAMPLE 14

Expression of pro-phthalyl amidase open reading frame in *Streptomyces lividans*

A 5 ml inoculum of *Streptomyces lividans* TK23/pZPA600 (grown for 48 hours at 30° C., 280 rpm) was added to each of two 2 L shake flasks containing 500 ml Trypticase Soy Broth medium and cultured at 30° C., 280 rpm for 24 hours. Incubations beyond 24 hours were deleterious to production of phthalyl amidase. Cells were removed by centrifugation (4° C., 15 min, 12,000×g) and phthalyl amidase activity in the cell-free broth was determined with compound III as substrate as in Example 13 (Table 14). The cell-free broth (800 ml, 0.10 mg/ml) was passed at 1 ml/min through a Mono Q column (10×10 mm (8 ml); Pharmacia). A linear gradient of 0 to 1.5M KCl in buffer A was passed over the column and 2 ml fractions were collected. Most of the phthalyl amidase activity eluted in fractions 19 and 20 (about 0.75M KCl).

A 1 ml aliquot of fraction 19 was concentrated 10-fold via ultrafiltration and analyzed by SDS-PAGE. A major protein band was observed at about 50,000 daltons, which corresponded to the molecular weight observed by electrospray mass spectrometry for purified mature phthalyl amidase obtained from *Xanthobacter agilis*. It also corresponded closely to the theoretical molecular weight predicted for a protein encoded by SEQ ID NO:1.

TABLE 14

| Expressing Organism | Plasmid | Specific Activity (nmol/min/mg) | Volumetric Activity (nmol/min/L) |
|---|---|---|---|
| *Xanthobacter agilis* | none | 63.0[a] | 3465[a] |
| *Escherichia coli* | pZPA400 | 0.96[b] | 438[b] |
| *Streptomyces* | pZPA600 | 748.8[b] | 76,378[b] |

TABLE 14-continued

| Expressing Organism | Plasmid | Specific Activity (nmol/min/mg) | Volumetric Activity (nmol/min/L) |
|---|---|---|---|
| lividans | | | |

Specific activity - units of enzyme/mg total protein
Volumetric activity - units of enzyme/liter of whole broth
Unit of enzyme - amount of enzyme that converts one nanomole of substrate in one minute
Phthalyl amidase is cell-bound for both *Xanchobacter agilis* and *Escherichia coli*; for *Streptomyces lividans* phthalyl amidase is secreted into the culture medium.
[a]Method of release by sonication as in Example 4A. See also Example 4B where method of release by lysozyme treatment.
[b]Method of assay as in Example 5.

EXAMPLE 15

Use of recombinant phthalyl amidase to remove the phthalyl blocking group from phthalamido carbacephem Activity was assayed by the addition of phthalyl amidase (30 μl of Mono Q fraction 19 from Example 14, 1.83 μg total protein) to 1.82 μg of compound III in a 1 ml reaction mixture buffered by 200 mM potassium phosphate, pH 8.2. The reaction was carried out at 32° C. for 20 minutes and stopped with the addition of 1 ml methanol. After removal of precipitate by centrifugation, an aliquot (30 μl) of the supernatant fraction was monitored by HPLC (254 nm absorbance) for both the carbacephem nucleus (XXXIV) and phthalic acid using a Zorbax C8 column (0.46×15 cm; MacMod Analytical Inc.). The reaction products were eluted by a mobile phase constructed as continuous mixed gradients from (a) 1% acetonitrile/0.2% trifluoroacetic acid and (b) 80% acetonitrile/0.2% trifluoroacetic acid. The above substrate, loracarbef nucleus, and phthalic acid eluted at 11.0, 3.4, and 5.9 minutes, respectively. HPLC peaks were identified and quantitated using data generated by known amounts of authentic compounds. The specific activity of recombinant phthalyl amidase derived from fraction 19 for conversion of substrate was 9.5 μmol/min/mg protein.

EXAMPLE 16

Use of recombinant phthalyl amidase to remove the phthalyl blocking group from phthalimido-aspartame In the synthesis of aspartame, the bivalent protection of the amino group of L-aspartic acid via a phthalimido moiety gives a superior substrate for a lyase-catalyzed condensation with L-phenylalanine methyl ester. However, an efficient method to convert the phthalimido-protected compound back to the amine was previously lacking. Following the condensation reaction, mild base was used to open the phthalimido moiety to a phthalamido moiety and recombinant phthalyl amidase was then used to catalyze hydrolysis of the latter to aspartame and phthalic acid (see Table 10).

We claim:

1. A DNA compound that comprises an isolated nucleotide sequence encoding SEQ ID NO:2.

2. The DNA compound of claim 1 wherein said isolated nucleotide sequence is SEQ ID NO:1.

3. The DNA compound of claim 1 that further comprises a signal peptide-encoding nucleotide sequence located adjacent to and upstream from said isolated nucleotide sequence.

4. The DNA compound of claim 3 wherein said signal peptide-encoding nucleotide sequence is endogenous to *Xanthobacter agilis*.

5. The DNA compound of claim 3 wherein said signal peptide-encoding nucleotide sequence is SEQ ID NO:8.

6. The DNA compound of claim 1 that further comprises a transcriptional termination sequence adjacent to and downstream from said isolated nucleotide sequence.

7. The DNA compound of claim 6 wherein said transcriptional termination sequence is SEQ ID NO:10.

8. A DNA compound that comprises an isolated nucleotide sequence encoding SEQ ID NO:4.

9. The DNA compound of claim 8 wherein said isolated nucleotide sequence is SEQ ID NO:3.

10. The DNA compound of claim 8 wherein said isolated nucleotide sequence is SEQ ID NO:5.

11. The DNA compound of claim 8 wherein said isolated nucleotide sequence is SEQ ID NO:6.

12. A recombinant DNA vector that comprises said isolated nucleotide sequence of claim 1.

13. The recombinant DNA vector of claim 12 that further comprises a promotor and translational activating sequence positioned to drive expression of said isolated nucleotide sequence.

14. The recombinant DNA vector of claim 13 wherein said promotor is endogenous to *Xanthobacter agilis*.

15. The recombinant DNA vector of claim 13 wherein said promotor is SEQ ID NO:7.

16. The recombinant DNA vector of claim 13 wherein said isolated nucleotide sequence is SEQ ID NO:1.

17. The recombinant DNA vector of claim 13 wherein said isolated nucleotide sequence is SEQ ID NO:3.

18. The recombinant DNA vector of claim 13 wherein said isolated nucleotide sequence is SEQ ID NO:5.

19. The recombinant DNA vector of claim 13 wherein said isolated nucleotide sequence is SEQ ID NO:6.

20. The recombinant DNA vector of claim 13 that is plasmid pZPA600.

21. The recombinant DNA vector of claim 13 that is plasmid pZPA400.

22. A bacterial host cell transformed with said DNA vector of claim 13.

23. A bacterial host cell transformed with said DNA vector of claim 16.

24. A bacterial host cell transformed with said DNA vector of claim 17.

25. A bacterial host cell transformed with said DNA vector of claim 18.

26. A bacterial host cell transformed with said DNA vector of claim 19.

27. A bacterial host cell transformed with said DNA vector of claim 20.

28. A bacterial host cell transformed with said DNA vector of claim 21.

29. The bacterial host cell of claim 22 selected from the group consisting of *Escherichia coli* and *Streptomyces lividans*.

30. The bacterial host cell of claim 29 that is *Streptomyces lividans*/pZPA600.

31. The bacterial host cell of claim 29 that is *Escherichia coli*/pZPA400.

32. A method for producing recombinant phthalyl amidase, said method comprising culturing a host cell of claim 22 under conditions suitable for gene expression, and recovering the expressed phthalyl amidase from the culture.

33. A method for producing recombinant phthalyl amidase, said method comprising culturing a host cell of claim 23 under conditions suitable for gene expression, and recovering the expressed phthalyl amidase from the culture.

34. A method for producing recombinant phthalyl amidase, said method comprising culturing a host cell of claim 24 under conditions suitable for gene expression, and recovering the expressed phthalyl amidase from the culture.

35. A method for producing recombinant phthalyl amidase, said method comprising culturing a host cell of claim 25 under conditions suitable for gene expression, and recovering the expressed phthalyl amidase from the culture.

36. A method for producing recombinant phthalyl amidase, said method comprising culturing a host cell of claim 26 under conditions suitable for gene expression, and recovering the expressed phthalyl amidase from the culture.

37. A method for producing recombinant phthalyl amidase, said method comprising culturing a host cell of claim 27 under conditions suitable for gene expression, and recovering the expressed phthalyl amidase from the culture.

38. A method for producing recombinant phthalyl amidase, said method comprising culturing a host cell of claim 28 under conditions suitable for gene expression, and recovering the expressed phthalyl amidase from the culture.

39. A method for producing recombinant phthalyl amidase, said method comprising culturing a host cell of claim 29 under conditions suitable for gene expression, and recovering the expressed phthalyl amidase from the culture.

40. A method for producing recombinant phthalyl amidase, said method comprising culturing a host cell of claim 30 under conditions suitable for gene expression, and recovering the expressed phthalyl amidase from the culture.

41. A method for producing recombinant phthalyl amidase, said method comprising culturing a host cell of claim 31 under conditions suitable for gene expression, and recovering the expressed phthalyl amidase from the culture.

42. The DNA compound of claim 1 wherein said isolated nucleotide sequence is SEQ ID NO:11.

* * * * *